United States Patent [19]

Kanamori

[11] Patent Number: 5,233,473
[45] Date of Patent: Aug. 3, 1993

[54] OPTICAL SYSTEM FOR ENDOSCOPES
[75] Inventor: Iwao Kanamori, Kanagawa, Japan
[73] Assignee: Olympus Optical Co., Ltd., Tokyo, Japan
[21] Appl. No.: 772,551
[22] Filed: Oct. 7, 1991
[30] Foreign Application Priority Data Oct. 9, 1990 [JP] Japan .................................. 2-269482

[51] Int. Cl.⁵ ............................ G02B 3/02; G02B 9/00
[52] U.S. Cl. .................................. 359/708; 359/716; 359/754
[58] Field of Search ........ 359/663, 708, 714, 691-692, 359/642, 656-661, 716-717, 728, 754, 784-797

[56] References Cited
U.S. PATENT DOCUMENTS

| | | | |
|---|---|---|---|
| 4,575,195 | 3/1986 | Hoogland | 359/716 |
| 4,867,546 | 9/1989 | Nishioka et al. | 359/714 |
| 4,957,355 | 9/1990 | Sato | 359/708 |
| 5,050,974 | 9/1991 | Takasugi et al. | 359/708 |
| 5,087,989 | 2/1992 | Igarashi | 359/708 |

FOREIGN PATENT DOCUMENTS 59-226315 12/1984 Japan .
3-39915 2/1991 Japan .

Primary Examiner—Bruce Y. Arnold
Assistant Examiner—Thong Nguyen
Attorney, Agent, or Firm—Cushman, Darby & Cushman

[57] ABSTRACT

An optical system for an endoscope has, in order from its object side, an objective lens system having a first lens unit with a negative refractive power, a second lens unit with a positive refractive power and an aspherical surface therein, and relay lens systems arranged on the image side of the objective lens system. The optical system for an endoscope can correct aberrations, assure uniform brightness over the entire range of an image from its center to its peripheral areas, and permits reducing the diameter of the cover glass plate used therein.

11 Claims, 12 Drawing Sheets $K_0 > K_{0.5} > K_1$ $K_0 < K_{0.5} < K_1$ $K_0 < K_{0.5} > K_1$ $K_0 > K_{0.5} < K_1$

I II III

OPTICAL SYSTEM FOR ENDOSCOPES

BACKGROUND OF THE INVENTION a) Field of the Invention

The present invention relates to an optical system for endoscopes to be use in medical and industrial fields, and more specifically to an optical system for endoscopes which is composed of an objective lens system and relay lens systems.

b) Description of the Prior Art

As an example of the conventional retrofocus type objective lens systems for endoscopes, there is known the objective lens system proposed by Japanese Patent Kokai Publication No. Sho 59-226315.

This conventional example is composed, as illustrated in FIG. 1, a first lens unit $L_1$ having a negative refractive power, an aperture stop S and a second lens unit $L_2$ having a positive refractive power which are arranged in order from the object side. The first lens unit $L_1$ has a negative refractive power for enlarging the visual field angle of the objective lens system and the second lens unit $L_2$ has an imaging function so as to compose a telecentric objective lens system which has a large field angle, the characteristic of an objective lens system for endoscopes, and allows the principal ray P to be incident perpendicularly on the image surface thereof at any image height.

Such an objective lens system for endoscopes 5 must be telecentric for preventing images transmitted through the relay lens systems from being darkened as described below: When a relay lens system which has an entrance pupil at infinite distance is arranged on the image surface of the objective lens system, rays are allowed to be incident on the relay lens system only within a certain range of angles and, if the principal ray P is incident obliquely on the image surface, transmission efficiency of light is lowered, thereby darkening an image transmitted through the relay lens system. Description will be made on a concrete optical system which is composed of the objective lens system shown in FIG. 1 and relay lens systems as illustrated in FIG. 2. An image $O_2$ formed by the objective lens system is transmitted by relay lens systems $R_1$, $R_2$ and $R_3$ as images $O_2$, $O_3$ and $O_4$, and at the same time, pupils which determine brightness of the images are also transmitted. These pupils are located at the position S in the objective lens system and the positions $S_1$, $S_2$, $S_3$, in the relay lens systems, and sizes of the pupils are determined, in most cases, nearly by outside diameters of the relay lens systems. Therefore, it is not always necessary to arrange an aperture stop in the objective lens system.

Further, the case of an objective lens system for endoscopes comprising a visual field changing prism $P_1$, it is difficult to arrange an aperture stop S in this objective lens system due to the fact that the visual field direction changing prism P: is arranged in the vicinity of the location at which the aperture stop S is to be arranged. It is therefore convenient to combine relay lens systems with the objective lens system which hardly allows arrangement of an aperture stop therein with relay lens systems.

As a conventional example of an optical system composed of an objective lens system for endoscopes and relay lens systems, there is known the optical system disclosed by Japanese Patent Kokai Publication No. Hei 3-39915. This optical system adopts a retrofocus type objective lens system comprising a lens component $L_1$ having an aspherical surface disposed thereon and a negative refractive power and a lens unit $L_2$ having a positive refractive power as illustrated in FIG. 4. This objective lens system, which is its same in the fundamental composition as the objective lens system disclosed by Japanese Patent Kokai Publication No. Sho 59-226315, uses an aspherical surface ASP in a first lens unit $L_1$ which is designed to satisfy a relation expressed by the following formula (i):

$$I = f \tan \theta_1 \qquad (i)$$

wherein the reference symbol I represents image height, the reference symbol f designates the focal length of the objective lens system and the reference symbol $\theta_1$ denotes the angle formed between the optical axis and the ray incident on the aspherical surface.

Further, said objective lens system comprises a second lens unit $L_2$ which is designed to satisfy a relation expressed by the following formula (ii):

$$I = f_2 \sin \theta_2 \qquad (ii)$$

wherein the reference symbol $f_2$ represents the focal length of the second lens unit $L_2$ and the reference symbol $\theta_2$ designates the angle formed between the optical axis and the ray incident on the object side surface of the second lens unit $L_2$.

The retrofocus type objective lens system for endoscopes which was known before the objective lens system described above was designed to satisfy the sine condition $I = f \sin \theta_1$, whereas the above-described objective lens system satisfies the condition $I = f \tan \theta_1$ by using the aspherical surface for correcting the distortion which is aggravated abruptly as visual field angle $\omega$ is widened. Further, the second lens unit $L_2$ of the above-described objective lens system is designed to satisfy the sine condition for maintaining uniform brightness over the entire range of an image from the center to the marginal portion thereof.

The objective lens system disclosed by above-mentioned Japanese Patent Kokai Publication No. Hei 3-39915 can have corrected distortion and a widened visual field angle. When the visual field angle of this objective lens system is further widened, however, a large angle is formed between the optical axis and the principal ray in a light bundle travelling from the aspherical surface toward the object side. When a cover glass plate CG is arranged on the object side of the aspherical surface ASP as shown in FIG. 4, for example, a ray having a high image height passes through a portion of the cover glass plate CG which is far from the optical axis and the cover glass plate CG must have a large outside diameter larger than that of the objective lens system which is restricted for use with endoscopes, thereby making the objective lens system unsuited for use with endoscopes.

As a means for bringing the ray passing through the cover glass plate CG nearer the optical axis, it is conceivable to displace the location of the aperture stop S nearer the cover glass plate CG as shown in FIG. 5. When the aperture stop S is brought nearer the cover glass plate CG, however, a ray having a high image height passes through the aspherical surface ASP of the first lens unit $L_1$ at a portion which is also brought nearer the optical axis and it is necessary for satisfying the relationship of $I = f \tan \theta_1$ to design the aspherical surface so as to have a shape which abruptly varies as the portions of said aspherical surface are farther from the optical axis. It is practically very difficult to form an aspherical surface of such a shape on a lens element having a small outside diameter.

FIG. 6 exemplifies concrete shapes of aspherical surfaces which are to be used for designing objective lens systems which have focal lengths on the order of 1 mm, visual field angle ω of 43.2° (2ω=86.4°) and distortion DT of different amounts. As is understood from this drawing, the aspherical surface must have shapes which are in practice difficult to form for obtaining distortion DT of −10% to −15% in the objective lens system.

SUMMARY OF THE INVENTION

A primary object of the present invention is to provide an optical system for endoscopes capable of correcting distortion which is abruptly aggravated as visual field angle is widened, assuring brightness uniform over the entire range of an image from the center to the marginal portion thereof, nevertheless requiring no enlargement of outside diameter of a cover glass plate beyond the restriction imposed on the outside diameters of endoscopes and using an aspherical surface having a shape which can easily be formed in practice.

The optical system for endoscopes according to the present invention is composed of an objective lens system having the composition illustrated in FIG. 7 and relay lens systems arranged on the image side of said objective lens system as shown in FIG. 8. That is to say, the optical system for endoscopes according to the present invention consists of an objective lens system which comprises, in the order from the object side, a first lens unit $L_1$ having a negative refractive power, an imaginary aperture stop and a second lens unit $L_2$ having a positive refractive power, and relay lens systems $R_1$ through $R_5$ and uses at least one aspherical surface in said second lens unit $L_2$.

The objective lens system used in the optical system for endoscopes according to the present invention is its same in the fundamental composition as the objective lens system illustrated in FIG. 1 and has a visual field angle ω which is widened by the function of the first lens unit $L_1$. Further, the imaginary aperture stop is arranged at a location which is brought as near the cover glass plate as possible to prevent the height of a ray from being enhanced on the cover glass plate by the widening of the visual field angle. Furthermore, an aspherical surface is used in the second lens unit $L_2$ for correcting distortion.

Distortion can be controlled by using an aspherical surface since curvature at a point on an aspherical surface can be continuously varied and it is therefore possible to vary curvature at a point on the aspherical surface through which the principal ray to attain to an optional point on an image passes.

FIG. 9A and FIG. 9B show diagrams illustrating shapes of aspherical surfaces and conditions of the principal rays P refracted by the surfaces.

When the angle of incidence of the principal ray P on the aspherical surface ASP is represented by $\theta_1$ and the angle of emergence thereof is designated by $\theta_2$, K is defined by the following formula:

$$\frac{\sin \theta_2}{\tan \theta_1} = K$$

Variation of the value of above-mentioned K is related to variation of distortion as described below:

The principal ray P shown in FIG. 9A has a large value of K and the principal ray P shown in FIG. 9B has a small value of K, but these principal rays have the same angle of emergence $\theta_2$. Let us assume that the principal rays P are to attain optimal image heights. The principal ray having a value of K which is enlarged from the center of image toward the marginal portion thereof produces positive distortion, whereas the principal ray having a value of K which is reduced from the center of image toward the marginal portion thereof produces negative distortion. The variations of the value of K and conditions of distortion are visualized in FIG. 10A, FIG. 10B, FIG. 10C and FIG. 10D. In these drawings, the reference symbols $K_0$, $K_{0.5}$ and $K_1$ represent the value of K at the image center, the value of K at 50% of the maximum image height and the value of K at the maximum image height respectively.

Now, description will be made on the brightness uniform over the entire range of an image from the center to the marginal portion thereof, which is to be accomplished as one of the objects of the present invention.

Since an optical system which is composed of an objective lens system and relay lens systems, like the optical system according to the present invention, scarcely comprises an aperture stop, brightness of an image formed by the optical system is determined by the aperture stops arranged in the relay lens systems.

The brightness of image determined by the aperture stops arranged in the relay lens systems is illustrated in FIG. 11A, FIG. 11B and FIG. 11C. FIG. 11A shows behavior of a ray to attain to the optical axis on the image (center of the image), FIG. 11B shows behavior of a ray to attain to 70% of the maximum image height, and FIG. 11C shows a behavior of ray to attain to the maximum image height. As is seen from these drawings, angles NA which are formed between the principal rays and the rays allowed to be incident on the relay lens systems out of the rays to attain to the different image heights are nearly equal to one another in FIG. 11A, FIG. 11B and FIG. 11C, and brightness on the image surfaces is nearly uniform regardless of image heights. Accordingly, the second lens unit $L_2$ need not satisfy the relationship expressed by the formula (i) in the optical system according to the present invention which does not comprise an aperture stop and determines brightness of image by the relay lens systems, unlike the conventional example already described above. The optical system according to the present invention therefore permits arranging an aspherical surface in the second lens unit.

Then, the optical system for endoscopes according to the present invention should desirably satisfy the following condition (1):

$$0.3 < L_A/L_0 \tag{1}$$

wherein the reference symbol $L_A$ represents the distance as measured along the optical axis from the object side or first surface of the optical system to the aspherical surface and the reference symbol $L_0$ designates the distance as measured along the optical axis from the first surface of the optical system to the image $O_1$ formed by the objective lens system.

The condition (1) defines the location of the aspherical surface relative to the length of the objective lens system. If the limit of the condition (1) is exceeded, the aspherical surface arranged in the second lens unit $L_2$ is brought neared the imaginary aperture stops and the rays to attain to the different image heights are brought closer to one another on the aspherical surface, thereby making it impossible to correct the distortion. In order to correct the distortion by the aspherical surface as already described above, it is necessary to vary curvature among the portions of the aspherical surface through which the rays to attain to the different image heights passes. When the rays to attain to the different image heights are brought close to one another on the aspherical surface, however, it is difficult to vary curvature on the aspherical surface for these rays.

Further, it is desirable that the objective lens system to be used in the optical system for endoscopes according to the present invention satisfies the following condition (2):

$$(2) \quad 0.1 < \frac{DT_A/DT_S}{L_S/L_0}$$

wherein the reference symbol $DT_A$ represents the distortion to be produced by the objective lens system at the maximum image height, the reference symbol $DT_S$ designates a value determined as $DT_S = \cos\omega - 1$ when the visual field angle at the maximum image height is represented by $\omega$ and the reference symbol LS denotes the distance as measured along the optical axis from the first surface of the optical system, to the imaginary aperture stop.

The condition (2) defines the location of the imaginary aperture stop arranged in the objective lens system relative to ratio of correction of the distortion. If the limit of the condition (2) is exceeded, the distortion can be corrected, but the imaginary aperture stop will be far from the first lens unit in the objective lens system, whereby rays will be high on the first lens unit and the cover glass plate will undesirably have an outside diameter exceeding the restriction imposed on the outside diameter of the optical system to be used with endoscopes.

Due to the restrictions imposed on the outside diameter and the number of lens elements, the objective lens system for endoscopes should desirably be of the retrofocus type and satisfy the sine condition. When the objective lens system for endoscopes satisfies these conditions, the following relationship establishes between distortion DT and visual field angle $\omega$:

$$DT = \cos\omega - 1$$

wherein the reference symbol DT represents a quotient in percent calculated by the following formula:

$$DT = \frac{y - y_0}{y_0} \times 100 \, (\%)$$

wherein the reference symbol y represents a size of an image deformed due to distortion, the reference symbol $y_0$ designates a size of an ideal image calculated by the paraxial theory.

When both the sine condition and the relationship between distortion and visual field angle are satisfied an ordinary objective lens system which has no spherical surface produces negative distortion (barrel type distortion) as listed in the table shown below:

| Visual field angle (2$\omega$) | 40° | 60° | 80° | 100° | 120° | 140° |
|---|---|---|---|---|---|---|
| Distortion (DT) | −6 | −14 | −23 | −36 | −50 | −66 (%) |

An image formed by the objective lens system or endoscopes which produces such negative distortion is deformed since a length on a marginal portion becomes shorter than a length at a central portion which should originally be the same as the length on the marginal portion. Therefore, it is impossible to measure or analyze shapes of objects accurately by using the objective lens system which produces such negative distortion for inspections of industrial products. Further, erroneous diagnoses may result by applying this objective lens system to medical fields.

In the objective lens system according to the present invention, an aspherical surface is used for correcting the negative distortion. The aspherical surface to be used in the objective lens system according to the present invention has a shape which is expressed by the formula (A) shown below, and satisfies the following condition (3) when a focal length of the objective lens is taken as 1:

$$x = \frac{Cy^2}{1 + \sqrt{1 - C^2y^2}} + Ey^4 + Fy^6 + Gy^8 + \ldots \quad (A)$$

$$(3) \quad |C| < 1$$

wherein the optical axis is taken as the abscissa for which the direction toward the image taken as positive, the intersection between the aspherical surface and the optical axis is taken as the origin, the direction perpendicular to the optical axis is taken as the ordinate, the reference symbols x and y represent values on the abscissa and the ordinate respectively, the reference symbol C designates an inverse number of a radius of curvature on a spherical surface in contact with the aspherical surface in the vicinity of the optical axis (reference sphere), and the reference symbols E, F, G, ... denote the aspherical surface coefficients of the fourth, sixth, eighth, ... orders respectively. When all of E, F, G, ... are zero, the formula (A) expresses a spherical surface.

If $|C|$ is larger than 1 in the above-mentioned condition (3), the radius of curvature will be too small for forming the aspherical surface in practice.

FIG. 12A and FIG. 12B show shapes of an aspherical surface which is to be used as the surface $r_{11}$ in the objective lens system illustrated in FIG. 6. FIG. 12A shows shapes of an aspherical surface corresponding to a visual field angle $\omega = 30°$, whereas FIG. 12B shows shapes of an aspherical surface corresponding to a visual field angle $\omega = 43.2°$, and the reference symbols DT(1), DT(0.8), used in these drawings represent shapes having values of $DT_A/DT_S$ of 1, 0.8, ... respectively.

The aspherical lens element should desirably be manufactured by molding glass, plastic or the similar material which has a low melting temperature. The aspherical surface should desirably be used in place of a planar surface or a curved surface having a large radius of curvature, and must satisfy the above-mentioned condition (3).

From the viewpoint of molding, the aspherical surface should desirably satisfy the following condition (4):

$$|X_A - X_S| < 1.5 \quad (4)$$

wherein the reference symbol $X_A$ represents a value of x on the aspherical surface corresponding to an optional value of y determined by the formula (A) and the reference symbol $X_S$ designates a value of x which is on the spherical surface (reference sphere) determined by C and corresponds to the value of y determined by the formula (A); both the values to be 7 determined on the basis of the focal length f of the objective lens system normalized to 1.

If the condition (4) is not satisfied, it will be difficult in practice to manufacture dies for molding the aspherical lens element and to manufacture the aspherical lens element by polishing.

DETAILED DESCRIPTION OF THE PREFERRED EMBODIMENTS

Figure 1:
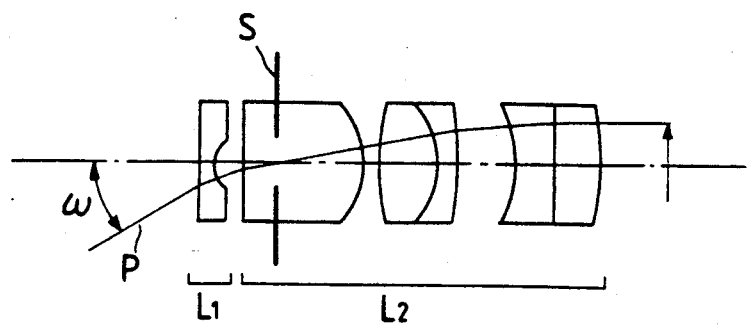
FIG. 1 through FIG. 4 show sectional views illustrating the conventional objective lens systems for endoscopes.
Figure 2:
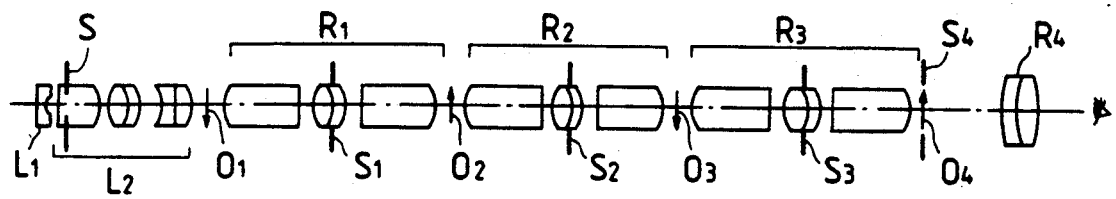
Figure 3:
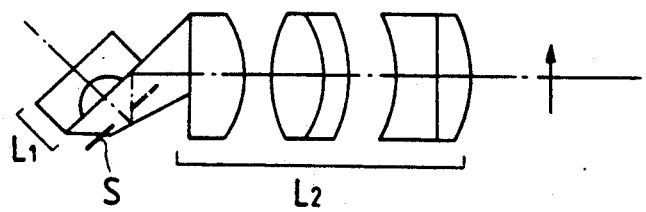
Figure 4:
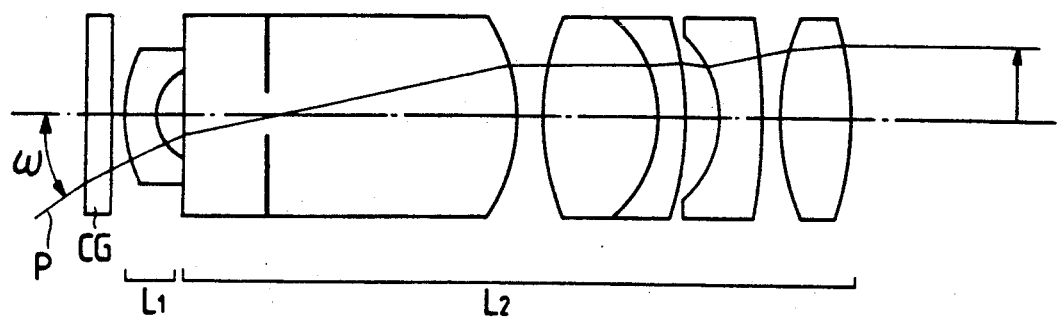
Figure 5:
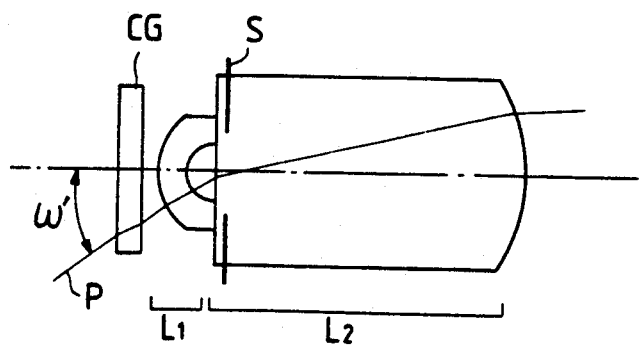
FIG. 5 shows a sectional view illustrating behavior of a principal ray in an optical system wherein a cover glass plate is arranged close to an objective lens system.
Figure 6:
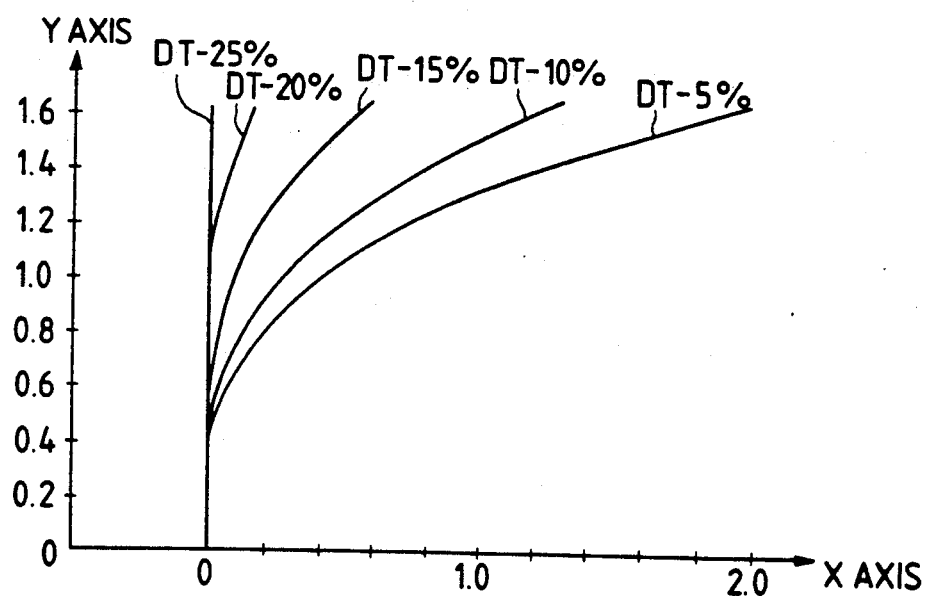
FIG. 6 shows graphs illustrating shapes of an aspherical surface to be used for correcting distortion.

Now, the present invention will be described more detailedly below with reference to the preferred embodiments illustrated in the accompanying drawings and given in the form of the following numerical data:

EMBODIMENT 1

| $f = 1.492,$ | $IH = 0.839,$ | $2\omega = 60°$ | |
|---|---|---|---|
| $r_1 = \infty$ | $d_1 = 0.2568$ | $n_1 = 1.51633$ | $\nu_1 = 64.15$ |
| $r_2 = \infty$ | $d_2 = 0.1712$ | | |
| $r_3 = \infty$ | $d_3 = 0.1712$ | $n_2 = 1.78800$ | $\nu_2 = 47.43$ |
| $r_4 = 1.5170$ | $d_4 = 0.24568$ | | |
| $r_5 = \infty$ | $d_5 = 0.6218$ | $n_3 = 1.78800$ | $\nu_3 = 47.43$ |

-continued

| $f = 1.492,$ | $IH = 0.839,$ | $2\omega = 60°$ | |
|---|---|---|---|
| $r_6 = \infty$ | $d_6 = 2.2464$ | $n_4 = 1.78800$ | $\nu_4 = 47.43$ |
| $r_7 = 318.5083$ | $d_7 = 0.2568$ | | |
| $r_8 = 2.6974$ | $d_8 = 1.6610$ | $n_5 = 1.64000$ | $\nu_5 = 60.09$ |
| $r_9 = -1.4555$ | $d_9 = 0.4281$ | $n_6 = 1.84666$ | $\nu_6 = 23.88$ |
| $r_{10} = -2.1319$ | $d_{10} = 0.856$ | | |
| (aspherical surface) | | | |
| $r_{11} = 5.6192$ | $d_{11} = 0.4281$ | $n_7 = 1.72825$ | $\nu_7 = 28.46$ |
| $r_{12} = 2.4376$ | $d_{12} = 1.7038$ | $n_8 = 1.77250$ | $\nu_8 = 49.66$ |
| $r_{13} = 5.8926$ | $d_{13} = 3.4247$ | | |
| $r_{14} = 9.7389$ | $d_{14} = 20.5479$ | $n_9 = 1.62004$ | $\nu_9 = 36.25$ |
| $r_{15} = \infty$ | $d_{15} = 1.4469$ | | |
| $r_{16} = 13.2329$ | $d_{16} = 2.2688$ | $n_{10} = 1.65160$ | $\nu_{10} = 58.67$ |
| $r_{17} = -2.9897$ | $d_{17} = 1.1558$ | $n_{11} = 1.80610$ | $\nu_{11} = 40.95$ |
| $r_{18} = -6.6781$ | $d_{18} = 2.4058$ | | |
| $r_{19} = \infty$ | $d_{19} = 20.5479$ | $n_{12} = 1.62004$ | $\nu_{12} = 36.25$ |
| $r_{20} = -9.7380$ | $d_{20} = 3.4247$ | | |
| $r_{21} = \infty$ | $d_{19} = 20.5479$ | $n_{13} = 1.62004$ | $\nu_{13} = 36.25$ |
| $r_{22} = \infty$ | $d_{22} = 1.4469$ | | |
| $r_{23} = 13.2329$ | $d_{23} = 2.2688$ | $n_{14} = 1.65160$ | $\nu_{14} = 58.67$ |
| $r_{24} = -2.9897$ | $d_{24} = 1.1558$ | $n_{15} = 1.80610$ | $\nu_{15} = 40.95$ |
| $r_{25} = 2.4058$ | | | |
| $r_{26} = \infty$ | $d_{26} = 20.5479$ | $n_{16} = 1.62004$ | $\nu_{16} = 36.25$ |
| $r_{27} = -9.7389$ | $d_{27} = 3.4247$ | | |
| $r_{28} = 9.7389$ | $d_{28} = 20.5479$ | $n_{17} = 1.62004$ | $\nu_{17} = 36.25$ |
| $r_{29} = \infty$ | $d_{29} = 1.4469$ | | |
| $r_{30} = 13.2329$ | $d_{30} = 2.2688$ | $n_{18} = 1.65160$ | $\nu_{18} = 58.67$ |
| $r_{31} = -2.9897$ | $d_{31} = 1.1558$ | $n_{19} = 1.80610$ | $\nu_{19} = 40.95$ |
| $r_{32} = -6.6781$ | $d_{32} = 2.4058$ | | |
| $r_{33} = \infty$ | $d_{33} = 20.5479$ | $n_{20} = 1.62004$ | $\nu_{20} = 36.25$ |
| $r_{34} = -9.7389$ | $d_{34} = 3.4247$ | | |
| $r_{35} = 9.7389$ | $d_{35} = 20.5479$ | $n_{21} = 1.62004$ | $\nu_{21} = 36.25$ |
| $r_{36} = \infty$ | $d_{36} = 1.4469$ | | |
| $r_{37} = 13.2329$ | $d_{37} = 2.2688$ | $n_{22} = 1.65160$ | $\nu_{22} = 58.67$ |
| $r_{38} = -2.9897$ | $d_{38} = 1.1558$ | $n_{23} = 1.80610$ | $\nu_{23} = 40.95$ |
| $r_{39} = -6.6781$ | $d_{39} = 2.4058$ | | |
| $r_{40} = \infty$ | $d_{40} = 20.5479$ | $n_{24} = 1.62004$ | $\nu_{24} = 36.25$ |
| $r_{41} = -3.4247$ | $d_{41} = 3.4247$ | | |
| $r_{42} = 9.7389$ | $d_{42} = 20.5479$ | $n_{25} = 1.62004$ | $\nu_{25} = 36.25$ |
| $r_{43} = \infty$ | $d_{43} = 1.4469$ | | |
| $r_{44} = 13.2329$ | $d_{44} = 2.2688$ | $n_{26} = 1.65160$ | $\nu_{26} = 58.67$ |
| $r_{45} = -2.9897$ | $d_{45} = 1.1558$ | $n_{27} = 1.80610$ | $\nu_{27} = 40.95$ |
| $r_{46} = -6.6781$ | $d_{46} = 2.4058$ | | |
| $r_{47} = \infty$ | $d_{47} = 18.5616$ | $n_{28} = 1.62004$ | $\nu_{28} = 36.25$ |
| $r_{48} = \infty$ | $d_{48} = 1.8579$ | $n_{29} = 1.51633$ | $\nu_{29} = 64.15$ |
| $r_{49} = -21.6036$ | | | | apsherical surface coefficients
$E = 0.29800 \times 10^{-1}$
$F = 0.11706 \times 10^{-6}, G = 0.14810 \times 10^{-11}$
$DT = -2\%, L_A/L_0 = 0.607$ $$\frac{DT_A/DT_S}{L_S/L_0} = 1.22$$

$\left. \begin{array}{l} |C| = 0.6998 \\ |X_A - X_S| = 0.3802 \end{array} \right\} \quad (f = 1)$

EMBODIMENT 2

| $f = 0.947,$ | $IH = 0.7466,$ | $2\omega = 86.4°$ | |
|---|---|---|---|
| $r_1 = \infty$ | $d_1 = 0.2285$ | $n_1 = 1.51633$ | $\nu_1 = 64.15$ |
| $r_2 = \infty$ | $d_2 = 0.1524$ | | |
| $r_3 = \infty$ | $d_3 = 0.1524$ | $n_2 = 1.78800$ | $\nu_2 = 47.43$ |
| $r_4 = 0.7016$ | $d_4 = 0.2285$ | | |
| $r_5 = \infty$ | $d_5 = 0.7016$ | $n_3 = 1.78800$ | $\nu_3 = 47.43$ |
| $r_6 = \infty$ (stop) | $d_6 = 3.1075$ | $n_4 = 1.78800$ | $\nu_4 = 47.43$ |
| $r_7 = -1.8861$ | $d_7 = 0.0762$ | | |
| $r_8 = -10.5334$ | $d_8 = 1.0742$ | $n_5 = 1.64000$ | $\nu_5 = 60.09$ |
| $r_9 = -1.2951$ | $d_9 = 0.7847$ | $n_6 = 1.84666$ | $\nu_6 = 23.88$ |
| $r_{10} = -2.0817$ | $d_{10} = 0.7364$ | | |
| (aspherical surface) | | | |
| $r_{11} = 3.9154$ | $d_{11} = 0.4495$ | $n_7 = 1.72825$ | $\nu_7 = 28.46$ |
| $r_{12} = 1.2066$ | $d_{12} = 0.7847$ | $n_8 = 1.77250$ | $\nu_8 = 49.66$ |
| $r_{13} = 2.1283$ | $d_{13} = 3.0473$ | | |
| $r_{14} = 18.2835$ | $d_{14} = 18.2835$ | $n_9 = 1.62004$ | $\nu_9 = 36.25$ |
| $r_{15} = \infty$ | $d_{15} = 1.2875$ | | |
| $r_{16} = 2.0188$ | $n_{10} = 1.65160$ | $\nu_{10} = 58.67$ | |

-continued

| f = 0.947, | IH = 0.7466, | 2ω = 86.4° |  |
|---|---|---|---|
| $r_{17} = -2.6603$ | $d_{17} = 1.0284$ | $n_{11} = 1.80610$ | $\nu_{11} = 40.95$ |
| $r_{18} = -5.9421$ | $d_{18} = 2.1407$ | | |
| $r_{19} = \infty$ | $d_{19} = 18.2835$ | $n_{12} = 1.62004$ | $\nu_{12} = 36.25$ |
| $r_{20} = -8.6656$ | $d_{20} = 3.0473$ | | |
| $r_{21} = 8.6656$ | $d_{21} = 18.2835$ | $n_{13} = 1.62004$ | $\nu_{13} = 36.25$ |
| $r_{22} = \infty$ | $d_{22} = 1.2875$ | | |
| $r_{23} = 11.7746$ | $d_{23} = 2.0188$ | $n_{14} = 1.65160$ | $\nu_{14} = 58.67$ |
| $r_{24} = -2.6603$ | $d_{24} = 1.0284$ | $n_{15} = 1.80610$ | $\nu_{15} = 40.95$ |
| $r_{25} = -5.9421$ | $d_{25} = 2.1407$ | | |
| $r_{26} = \infty$ | $d_{26} = 18.2835$ | $n_{16} = 1.62004$ | $\nu_{16} = 36.25$ |
| $r_{27} = -8.6656$ | $d_{27} = 3.0473$ | | |
| $r_{28} = 8.6656$ | $d_{28} = 18.2835$ | $n_{17} = 1.62004$ | $\nu_{17} = 36.25$ |
| $r_{29} = \infty$ | $d_{29} = 1.2875$ | | |
| $r_{30} = 11.7746$ | $d_{30} = 2.0188$ | $n_{18} = 1.65160$ | $\nu_{18} = 58.67$ |
| $r_{31} = -2.6603$ | $d_{31} = 1.0284$ | $n_{19} = 1.80610$ | $\nu_{19} = 40.95$ |
| $r_{32} = -5.9421$ | $d_{32} = 2.1407$ | | |
| $r_{33} = \infty$ | $d_{33} = 18.2835$ | $n_{20} = 1.62004$ | $\nu_{20} = 36.25$ |
| $r_{34} = -8.6656$ | $d_{34} = 3.0473$ | | |
| $r_{35} = 8.6656$ | $d_{35} = 18.2835$ | $n_{21} = 1.62004$ | $\nu_{21} = 36.25$ |
| $r_{36} = \infty$ | $d_{36} = 1.2875$ | | |
| $r_{37} = 11.7746$ | $d_{37} = 2.0188$ | $n_{22} = 1.65160$ | $\nu_{22} = 58.67$ |
| $r_{38} = -2.6603$ | $d_{38} = 1.0284$ | $n_{23} = 1.80610$ | $\nu_{23} = 40.95$ |
| $r_{39} = -5.9421$ | $d_{39} = 2.1407$ | | |
| $r_{40} = \infty$ | $d_{40} = 18.2835$ | $n_{24} = 1.62004$ | $\nu_{24} = 36.25$ |
| $r_{41} = -8.6656$ | $d_{41} = 3.0473$ | | |
| $r_{42} = 8.6656$ | $d_{42} = 18.2835$ | $n_{25} = 1.62004$ | $\nu_{25} = 36.25$ |
| $r_{43} = \infty$ | $d_{43} = 1.2875$ | | |
| $r_{44} = 11.7746$ | $d_{44} = 2.0188$ | $n_{26} = 1.65160$ | $\nu_{26} = 58.67$ |
| $r_{45} = -2.6603$ | $d_{45} = 1.0284$ | $n_{27} = 1.80610$ | $\nu_{27} = 40.95$ |
| $r_{46} = -5.9421$ | $d_{46} = 2.1407$ | | |
| $r_{47} = \infty$ | $d_{47} = 16.5161$ | $n_{28} = 1.62004$ | $\nu_{28} = 36.25$ |
| $r_{48} = \infty$ | $d_{48} = 1.6531$ | $n_{29} = 1.51633$ | $\nu_{29} = 64.15$ |
| $r_{49} = -19.2228$ | | | | aspherical surface coefficients
$E = 0.18567 \times 10^{-1}$
$F = 0.93770 \times 10^{-7}, G = 0.14179 \times 10^{-11}$
$DT = -15\%, L_A/L_0 = 0.651$ $$\frac{DT_A/DT_S}{L_S/L_0} = 4.11$$

$|C| = 0.455, |X_A - X_S| = 0.1655 \ (f = 1)$

EMBODIMENT 3

| f = 0.834, | IH = 0.7351, | 2ω = 100° |  |
|---|---|---|---|
| $r_1 = \infty$ | $d_1 = 0.2250$ | $n_1 = 1.51633$ | $\nu_1 = 64.15$ |
| $r_2 = \infty$ | $d_2 = 0.1500$ | | |
| $r_3 = \infty$ | $d_3 = 0.1500$ | $n_2 = 1.78800$ | $\nu_2 = 47.43$ |
| $r_4 = 0.5376$ | $d_4 = 0.2250$ | | |
| $r_5 = \infty$ | $d_5 = 0.6378$ | $n_3 = 1.78800$ | $\nu_3 = 47.43$ |
| $r_6 = \infty$ (stop) | $d_6 = 3.1128$ | $n_4 = 1.78800$ | $\nu_4 = 47.43$ |
| $r_7 = -1.9140$ | $d_7 = 0.0750$ | | |
| $r_8 = 69.6402$ | $d_8 = 1.3277$ | $n_5 = 1.63854$ | $\nu_5 = 55.38$ |
| $r_9 = -1.2752$ | $d_9 = 0.5251$ | $n_6 = 1.84666$ | $\nu_6 = 23.88$ |
| $r_{10} = -1.9409$ (aspherical surface) | $d_{10} = 0.5034$ | | |
| $r_{11} = 20.3978$ | $d_{11} = 0.5251$ | $n_7 = 1.72825$ | $\nu_7 = 28.46$ |
| $r_{12} = 1.9913$ | $d_{12} = 1.0427$ | $n_8 = 1.77250$ | $\nu_8 = 49.66$ |
| $r_{13} = 3.3243$ | $d_{13} = 3.0005$ | | |
| $r_{14} = 8.5327$ | $d_{14} = 18.0031$ | $n_9 = 1.62004$ | $\nu_9 = 36.25$ |
| $r_{15} = \infty$ | $d_{15} = 1.2677$ | | |
| $r_{16} = 11.5940$ | $d_{16} = 1.9878$ | $n_{10} = 1.65160$ | $\nu_{10} = 58.67$ |
| $r_{17} = -2.6194$ | $d_{17} = 1.0127$ | $n_{11} = 1.80610$ | $\nu_{11} = 40.95$ |
| $r_{18} = -5.8510$ | $d_{18} = 2.1079$ | | |
| $r_{19} = \infty$ | $d_{19} = 18.0031$ | $n_{12} = 1.62004$ | $\nu_{12} = 36.25$ |
| $r_{20} = -8.5327$ | $d_{20} = 3.0005$ | | |
| $r_{21} = 8.5327$ | $d_{21} = 18.0031$ | $n_{13} = 1.62004$ | $\nu_{13} = 36.25$ |
| $r_{22} = \infty$ | $d_{22} = 1.2677$ | | |
| $r_{23} = 11.5940$ | $d_{23} = 1.9878$ | $n_{14} = 1.65160$ | $\nu_{14} = 58.67$ |
| $r_{24} = -2.6194$ | $d_{24} = 1.0127$ | $n_{15} = 1.80610$ | $\nu_{15} = 40.95$ |
| $r_{25} = -5.8510$ | $d_{25} = 2.1079$ | | |
| $r_{26} = \infty$ | $d_{26} = 18.0031$ | $n_{16} = 1.62004$ | $\nu_{16} = 36.25$ |
| $r_{27} = -8.5327$ | $d_{27} = 3.0005$ | | |
| $r_{28} = 8.5327$ | $d_{28} = 18.0031$ | $n_{17} = 1.62004$ | $\nu_{17} = 36.25$ |
| $r_{29} = \infty$ | $d_{29} = 1.2677$ | | |
| $r_{30} = 11.5940$ | $d_{30} = 1.9878$ | $n_{18} = 1.65160$ | $\nu_{18} = 58.67$ |

-continued

| f = 0.834, | IH = 0.7351, | 2ω = 100° |  |
|---|---|---|---|
| $r_{31} = -2.6194$ | $d_{31} = 1.0127$ | $n_{19} = 1.80610$ | $\nu_{19} = 40.95$ |
| $r_{32} = -5.8510$ | $d_{32} = 2.1079$ | | |
| $r_{33} = \infty$ | $d_{33} = 18.0031$ | $n_{20} = 1.62004$ | $\nu_{20} = 36.25$ |
| $r_{34} = -8.5327$ | $d_{34} = 3.0005$ | | |
| $r_{35} = 8.5327$ | $d_{35} = 18.0031$ | $n_{21} = 1.62004$ | $\nu_{21} = 36.25$ |
| $r_{36} = \infty$ | $d_{36} = 1.2677$ | | |
| $r_{37} = 11.5940$ | $d_{37} = 1.9878$ | $n_{22} = 1.65160$ | $\nu_{22} = 58.67$ |
| $r_{38} = -2.6194$ | $d_{38} = 1.0127$ | $n_{23} = 1.80610$ | $\nu_{23} = 40.95$ |
| $r_{39} = -5.8510$ | $d_{39} = 2.1079$ | | |
| $r_{40} = \infty$ | $d_{40} = 18.0031$ | $n_{24} = 1.62004$ | $\nu_{24} = 36.25$ |
| $r_{41} = -8.5327$ | $d_{41} = 3.0005$ | | |
| $r_{42} = 8.5327$ | $d_{42} = 18.0031$ | $n_{25} = 1.62004$ | $\nu_{25} = 36.25$ |
| $r_{43} = 1.2677$ | $d_{44} = 1.9878$ | $n_{26} = 1.65160$ | $\nu_{26} = 58.67$ |
| $r_{45} = -2.6194$ | $d_{45} = 1.0127$ | $n_{27} = 1.80610$ | $\nu_{27} = 40.95$ |
| $r_{46} = -5.8510$ | $d_{46} = 2.1079$ | | |
| $r_{47} = \infty$ | $d_{47} = 16.2628$ | $n_{28} = 1.62004$ | $\nu_{28} = 36.25$ |
| $r_{48} = \infty$ | $d_{48} = 1.6278$ | $n_{29} = 1.51633$ | $\nu_{29} = 64.15$ |
| $r_{49} = -18.9280$ | | | | aspherical surface coefficients
$E = 0.22391 \times 10^{-1}$
$F = -0.63410 \times 10^{-8}, G = 0.69384 \times 10^{-13}$
$DT = -25\%, L_A/L_0 = 0.643$ $$\frac{DT_A/DT_S}{L_S/L_0} = 5.32$$

$|C| = 0.4297, |X_A - X_S| = 0.1364 \ (f = 1)$

EMBODIMENT 4

| f = 0.771, | IH = 0.7382, | 2ω = 110° |  |
|---|---|---|---|
| $r_1 = \infty$ | $d_1 = 0.2260$ | $n_1 = 1.51633$ | $\nu_1 = 64.15$ |
| $r_2 = \infty$ | $d_2 = 0.1507$ | | |
| $r_3 = \infty$ | $d_3 = 0.1507$ | $n_2 = 1.78800$ | $\nu_2 = 47.43$ |
| $r_4 = 0.4115$ | $d_4 = 0.2260$ | | |
| $r_5 = \infty$ | $d_5 = 0.3574$ | $n_3 = 1.78800$ | $\nu_3 = 47.43$ |
| $r_6 = \infty$ (stop) | $d_6 = 3.4091$ | $n_4 = 1.78800$ | $\nu_4 = 47.43$ |
| $r_7 = -2.0163$ | $d_7 = 0.0753$ | | |
| $r_8 = 5.0184$ | $d_8 = 1.3334$ | $n_5 = 1.63854$ | $\nu_5 = 55.38$ |
| $r_9 = -1.8171$ | $d_9 = 0.5273$ | $n_6 = 1.84666$ | $\nu_6 = 23.88$ |
| $r_{10} = -2.2332$ (aspherical surface) | $d_{10} = 0.4631$ | | |
| $r_{11} = -6.0563$ | $d_{11} = 0.5273$ | $n_7 = 1.72825$ | $\nu_7 = 28.46$ |
| $r_{12} = 1.0686$ | $d_{12} = 1.0471$ | $n_8 = 1.77250$ | $\nu_8 = 49.66$ |
| $r_{13} = 3.6977$ | $d_{13} = 3.0132$ | | |
| $r_{14} = 8.5689$ | $d_{14} = 18.0794$ | $n_9 = 1.62004$ | $\nu_9 = 36.25$ |
| $r_{15} = \infty$ | $d_{15} = 1.2731$ | | |
| $r_{16} = 11.6431$ | $d_{16} = 1.9963$ | $n_{10} = 1.65160$ | $\nu_{10} = 58.67$ |
| $r_{17} = -2.6305$ | $d_{17} = 1.0170$ | $n_{11} = 1.80610$ | $\nu_{11} = 40.95$ |
| $r_{18} = -5.8758$ | $d_{18} = 2.1168$ | | |
| $r_{19} = \infty$ | $d_{19} = 18.0794$ | $n_{12} = 1.62004$ | $\nu_{12} = 36.25$ |
| $r_{20} = -8.5689$ | $d_{20} = 3.0132$ | | |
| $r_{21} = 8.5689$ | $d_{21} = 18.0794$ | $n_{13} = 1.62004$ | $\nu_{13} = 36.25$ |
| $r_{22} = \infty$ | $d_{22} = 1.2731$ | | |
| $r_{23} = 11.6431$ | $d_{23} = 1.9963$ | $n_{14} = 1.65160$ | $\nu_{14} = 58.67$ |
| $r_{24} = -2.6305$ | $d_{24} = 1.0170$ | $n_{15} = 1.80610$ | $\nu_{15} = 40.95$ |
| $r_{25} = -5.8758$ | $d_{25} = 2.1168$ | | |
| $r_{26} = \infty$ | $d_{26} = 18.0794$ | $n_{16} = 1.62004$ | $\nu_{16} = 36.25$ |
| $r_{27} = -8.5689$ | $d_{27} = 3.0132$ | | |
| $r_{28} = 8.5689$ | $d_{28} = 18.0794$ | $n_{17} = 1.62004$ | $\nu_{17} = 36.25$ |
| $r_{29} = \infty$ | $d_{29} = 1.2731$ | | |
| $r_{30} = 11.6431$ | $d_{30} = 1.9963$ | $n_{18} = 1.65160$ | $\nu_{18} = 58.67$ |
| $r_{31} = -2.6305$ | $d_{31} = 1.0170$ | $n_{19} = 1.80610$ | $\nu_{19} = 40.95$ |
| $r_{32} = -5.8758$ | $d_{32} = 2.1168$ | | |
| $r_{33} = \infty$ | $d_{33} = 18.0794$ | $n_{20} = 1.62004$ | $\nu_{20} = 36.25$ |
| $r_{34} = -8.5689$ | $d_{34} = 3.0132$ | | |
| $r_{35} = 8.5689$ | $d_{35} = 18.0794$ | $n_{21} = 1.62004$ | $\nu_{21} = 36.25$ |
| $r_{36} = \infty$ | $d_{36} = 1.2731$ | | |
| $r_{37} = 11.6431$ | $d_{37} = 1.9963$ | $n_{22} = 1.65160$ | $\nu_{22} = 58.67$ |
| $r_{38} = -2.6305$ | $d_{38} = 1.0170$ | $n_{23} = 1.80610$ | $\nu_{23} = 40.95$ |
| $r_{39} = -5.8758$ | $d_{39} = 2.1168$ | | |
| $r_{40} = \infty$ | $d_{40} = 18.0794$ | $n_{24} = 1.62004$ | $\nu_{24} = 36.25$ |
| $r_{41} = -8.5689$ | $d_{41} = 3.0132$ | | |
| $r_{42} = 8.5689$ | $d_{42} = 18.0794$ | $n_{25} = 1.62004$ | $\nu_{25} = 36.25$ |
| $r_{43} = \infty$ | $d_{43} = 1.2731$ | | |
| $r_{44} = 11.6431$ | $d_{44} = 1.9963$ | $n_{26} = 1.65160$ | $\nu_{26} = 58.67$ |
| $r_{45} = -2.6305$ | $d_{45} = 1.0170$ | $n_{27} = 1.80610$ | $\nu_{27} = 40.95$ |

-continued $f = 0.771$, $IH = 0.7382$, $2\omega = 110°$

| | | | |
|---|---|---|---|
| $r_{46} = -5.8758$ | $d_{46} = 2.1168$ | | |
| $r_{47} = \infty$ | $d_{47} = 16.3317$ | $n_{28} = 1.62004$ | $\nu_{28} = 36.25$ |
| $r_{48} = \infty$ | $d_{48} = 1.6347$ | $n_{29} = 1.51633$ | $\nu_{29} = 64.15$ |
| $r_{49} = -19.0082$ | | | | aspherical surface coefficients
$E = 0.28058 \times 10^{-1}$
$F = -0.41412 \times 10^{-6}$, $G = -0.23294 \times 10^{-11}$
$DT = -32\%$, $L_A/L_0 = 0.646$ $$\frac{DT_A/DT_S}{L_S/L_0} = 7.03$$

$|C| = 0.3452$, $|X_A - X_X| = 0.135$ ($f = 1$)

EMBODIMENT 5

$f = 1.191$, $IH = 0.6693$, $2\omega = 60°$

| | | | |
|---|---|---|---|
| $r_1 = \infty$ | $d_1 = 0.2049$ | $n_1 = 1.51633$ | $\nu_1 = 64.15$ |
| $r_2 = \infty$ | $d_2 = 0.1366$ | | |
| $r_3 = \infty$ | $d_3 = 0.1366$ | $n_2 = 1.78800$ | $\nu_2 = 47.43$ |
| $r_4 = 0.8904$ | $d_4 = 0.2049$ | | |
| $r_5 = \infty$ | $d_5 = 0.5308$ | $n_3 = 1.78800$ | $\nu_3 = 47.43$ |
| $r_6 = \infty$ (stop) | $d_6 = 2.8840$ | $n_4 = 1.78800$ | $\nu_4 = 47.43$ |
| $r_7 = -2.2026$ | $d_7 = 0.2049$ | | |
| $r_8 = -12.5008$ | $d_8 = 1.3249$ | $n_5 = 1.64000$ | $\nu_5 = 60.09$ |
| $r_9 = -1.1610$ | $d_9 = 0.3415$ | $n_6 = 1.84666$ | $\nu_6 = 23.88$ |
| $r_{10} = -1.9261$ | $d_{10} = 0.9644$ | | |
| $r_{11} = 5.0616$ | $d_{11} = 0.3415$ | $n_7 = 1.72825$ | $\nu_7 = 28.46$ |
| (aspherical surface) | | | |
| $r_{12} = 13.1778$ | $d_{12} = 1.3591$ | $n_8 = 1.77250$ | $\nu_8 = 49.66$ |
| $r_{13} = 4.1719$ | $d_{13} = 2.7319$ | | |
| $r_{14} = 7.7687$ | $d_{14} = 16.3911$ | $n_9 = 1.62004$ | $\nu_9 = 36.25$ |
| $r_{15} = \infty$ | $d_{15} = 1.1542$ | | |
| $r_{16} = 10.5559$ | $d_{16} = 1.8099$ | $n_{10} = 1.65160$ | $\nu_{10} = 58.67$ |
| $r_{17} = -2.3849$ | $d_{17} = 0.9220$ | $n_{11} = 1.80610$ | $\nu_{11} = 40.95$ |
| $r_{18} = -5.3271$ | $d_{18} = 1.9191$ | | |
| $r_{19} = \infty$ | $d_{19} = 16.3911$ | $n_{12} = 1.62004$ | $\nu_{12} = 36.25$ |
| $r_{20} = -7.7687$ | $d_{20} = 2.7319$ | | |
| $r_{21} = 7.7687$ | $d_{21} = 16.3911$ | $n_{13} = 1.62004$ | $\nu_{13} = 36.25$ |
| $r_{22} = \infty$ | $d_{22} = 1.1542$ | | |
| $r_{23} = 10.5559$ | $d_{23} = 1.8099$ | $n_{14} = 1.65160$ | $\nu_{14} = 58.67$ |
| $r_{24} = -2.3849$ | $d_{24} = 0.9220$ | $n_{15} = 1.80610$ | $\nu_{15} = 40.95$ |
| $r_{25} = -5.3271$ | $d_{25} = 1.9191$ | | |
| $r_{26} = \infty$ | $d_{26} = 16.3911$ | $n_{16} = 1.62004$ | $\nu_{16} = 36.25$ |
| $r_{27} = -7.7687$ | $d_{27} = 2.7319$ | | |
| $r_{28} = 7.7687$ | $d_{28} = 16.3911$ | $n_{17} = 1.62004$ | $\nu_{17} = 36.25$ |
| $r_{29} = \infty$ | $d_{29} = 1.1542$ | | |
| $r_{30} = 10.5559$ | $d_{30} = 1.8099$ | $n_{18} = 1.65160$ | $\nu_{18} = 58.67$ |
| $r_{31} = -2.3849$ | $d_{31} = 0.9220$ | $n_{19} = 1.80610$ | $\nu_{19} = 40.95$ |
| $r_{32} = -5.3271$ | $d_{32} = 1.9191$ | | |
| $r_{33} = \infty$ | $d_{33} = 16.3911$ | $n_{20} = 1.62004$ | $\nu_{20} = 36.25$ |
| $r_{34} = -7.7687$ | $d_{34} = 2.7319$ | | |
| $r_{35} = 7.7687$ | $d_{35} = 16.3911$ | $n_{21} = 1.62004$ | $\nu_{21} = 36.25$ |
| $r_{36} = \infty$ | $d_{36} = 1.1542$ | | |
| $r_{37} = 10.5559$ | $d_{37} = 1.8099$ | $n_{22} = 1.65160$ | $\nu_{22} = 58.67$ |
| $r_{38} = -2.3849$ | $d_{38} = 0.9220$ | $n_{23} = 1.80610$ | $\nu_{23} = 40.95$ |
| $r_{39} = -5.3271$ | $d_{39} = 1.9191$ | | |
| $r_{40} = \infty$ | $d_{40} = 16.3911$ | $n_{24} = 1.62004$ | $\nu_{24} = 36.25$ |
| $r_{41} = -7.7687$ | $d_{41} = 2.7319$ | | |
| $r_{42} = 7.7687$ | $d_{42} = 16.3911$ | $n_{25} = 1.62004$ | $\nu_{25} = 36.25$ |
| $r_{43} = \infty$ | $d_{43} = 1.1542$ | | |
| $r_{44} = 10.5559$ | $d_{44} = 1.8099$ | $n_{26} = 1.65160$ | $\nu_{26} = 58.67$ |
| $r_{45} = -2.3849$ | $d_{45} = 0.9220$ | $n_{27} = 1.80610$ | $\nu_{27} = 40.95$ |
| $r_{46} = -5.3271$ | $d_{46} = 1.9191$ | | |
| $r_{47} = \infty$ | $d_{47} = 14.8066$ | $n_{28} = 1.62004$ | $\nu_{28} = 36.25$ |
| $r_{48} = \infty$ | $d_{48} = 1.4820$ | $n_{29} = 1.51633$ | $\nu_{29} = 64.15$ |
| $r_{49} = -17.2332$ | | | | aspherical surface coefficients
$E = -0.31317 \times 10^{-1}$
$F = -0.27640 \times 10^{-6}$, $G = -0.27204 \times 10^{-11}$
$DT = -2\%$, $L_A/L_0 = 0.693$ -continued $f = 1.191$, $IH = 0.6693$, $2\omega = 60°$ $$\frac{DT_A/DT_S}{L_S/L_0} = 1.49$$

$|C| = 0.2353$, $|X_A - X_S| = 0.5554$ ($f = 1$)

EMBODIMENT 6

$f = 0.973$, $IH = 0.7925$, $2\omega = 86.4°$

| | | | |
|---|---|---|---|
| $r_1 = \infty$ | $d_1 = 0.2426$ | $n_1 = 1.51633$ | $\nu_1 = 64.15$ |
| $r_2 = \infty$ | $d_2 = 0.1617$ | | |
| $r_3 = \infty$ | $d_3 = 0.1617$ | $n_2 = 1.78800$ | $\nu_2 = 47.43$ |
| $r_4 = 0.8059$ | $d_4 = 0.2426$ | | |
| $r_5 = \infty$ | $d_5 = 0.6783$ | $n_3 = 1.78800$ | $\nu_3 = 47.43$ |
| $r_6 = \infty$ (stop) | $d_6 = 3.3652$ | $n_4 = 1.78800$ | $\nu_4 = 47.43$ |
| $r_7 = -2.2620$ | $d_7 = 0.0809$ | | |
| $r_8 = 11.5345$ | $d_8 = 1.1403$ | $n_5 = 1.64000$ | $\nu_5 = 60.09$ |
| $r_9 = -1.3748$ | $d_9 = 0.8330$ | $n_6 = 1.84666$ | $\nu_6 = 23.88$ |
| $r_{10} = -2.4480$ | $d_{10} = 0.1662$ | | |
| $r_{11} = 3.3994$ | $d_{11} = 0.4771$ | $n_7 = 1.72825$ | $\nu_7 = 28.46$ |
| (aspherical surface) | | | |
| $r_{12} = 1.5146$ | $d_{12} = 0.8330$ | $n_8 = 1.77250$ | $\nu_8 = 49.66$ |
| $r_{13} = 2.0195$ | $d_{13} = 3.2348$ | | |
| $r_{14} = 9.1990$ | $d_{14} = 19.4089$ | $n_9 = 1.62004$ | $\nu_9 = 36.25$ |
| $r_{15} = \infty$ | $d_{15} = 1.3667$ | | |
| $r_{16} = 12.4993$ | $d_{16} = 2.1431$ | $n_{10} = 1.65160$ | $\nu_{10} = 58.67$ |
| $r_{17} = -2.8240$ | $d_{17} = 1.0918$ | $n_{11} = 1.80610$ | $\nu_{11} = 40.95$ |
| $r_{18} = -6.3079$ | $d_{18} = 2.2725$ | | |
| $r_{19} = \infty$ | $d_{19} = 19.4089$ | $n_{12} = 1.62004$ | $\nu_{12} = 36.25$ |
| $r_{20} = -9.1990$ | $d_{20} = 3.2348$ | | |
| $r_{21} = 9.1990$ | $d_{21} = 19.4089$ | $n_{13} = 1.62004$ | $\nu_{13} = 36.25$ |
| $r_{22} = \infty$ | $d_{22} = 1.3667$ | | |
| $r_{23} = 12.4993$ | $d_{23} = 2.1431$ | $n_{14} = 1.65160$ | $\nu_{14} = 58.67$ |
| $r_{24} = -2.8240$ | $d_{24} = 1.0918$ | $n_{15} = 1.80610$ | $\nu_{15} = 40.95$ |
| $r_{25} = -6.3079$ | $d_{25} = 2.2725$ | | |
| $r_{26} = \infty$ | $d_{26} = 19.4089$ | $n_{16} = 1.62004$ | $\nu_{16} = 36.25$ |
| $r_{27} = -9.1990$ | $d_{27} = 3.2348$ | | |
| $r_{28} = 9.1990$ | $d_{28} = 19.4089$ | $n_{17} = 1.62004$ | $\nu_{17} = 36.25$ |
| $r_{29} = \infty$ | $d_{29} = 1.3667$ | | |
| $r_{30} = 12.4993$ | $d_{30} = 2.1431$ | $n_{18} = 1.65160$ | $\nu_{18} = 58.67$ |
| $r_{31} = -2.8240$ | $d_{31} = 1.0918$ | $n_{19} = 1.80610$ | $\nu_{19} = 40.95$ |
| $r_{32} = -6.3079$ | $d_{32} = 2.2725$ | | |
| $r_{33} = \infty$ | $d_{33} = 19.4089$ | $n_{20} = 1.62004$ | $\nu_{20} = 36.25$ |
| $r_{34} = -9.1990$ | $d_{34} = 3.2348$ | | |
| $r_{35} = 9.1990$ | $d_{35} = 19.4089$ | $n_{21} = 1.62004$ | $\nu_{21} = 36.25$ |
| $r_{36} = \infty$ | $d_{36} = 1.3667$ | | |
| $r_{37} = 12.4993$ | $d_{37} = 2.1431$ | $n_{22} = 1.65160$ | $\nu_{22} = 58.67$ |
| $r_{38} = -2.8240$ | $d_{38} = 1.0918$ | $n_{23} = 1.80610$ | $\nu_{23} = 40.95$ |
| $r_{39} = -6.3079$ | $d_{39} = 2.2725$ | | |
| $r_{40} = \infty$ | $d_{40} = 19.4089$ | $n_{24} = 1.62004$ | $\nu_{24} = 36.25$ |
| $r_{41} = -9.1990$ | $d_{41} = 3.2348$ | | |
| $r_{42} = 9.1990$ | $d_{42} = 19.4089$ | $n_{25} = 1.62004$ | $\nu_{25} = 36.25$ |
| $r_{43} = \infty$ | $d_{43} = 1.3667$ | | |
| $r_{44} = 12.4993$ | $d_{44} = 2.1431$ | $n_{26} = 1.65160$ | $\nu_{26} = 58.67$ |
| $r_{45} = -2.8240$ | $d_{45} = 1.0918$ | $n_{27} = 1.80610$ | $\nu_{27} = 40.95$ |
| $r_{46} = -6.3079$ | $d_{46} = 2.2725$ | | |
| $r_{47} = \infty$ | $d_{47} = 17.5327$ | $n_{28} = 1.62004$ | $\nu_{28} = 36.25$ |
| $r_{48} = \infty$ | $d_{48} = 1.7549$ | $n_{29} = 1.51633$ | $\nu_{29} = 64.15$ |
| $r_{49} = -20.4060$ | | | | aspherical surface coefficients
$E = -0.25247 \times 10^{-1}$
$F = -0.57857 \times 10^{-8}$, $G = 0.26734 \times 10^{-13}$
$DT = -12\%$, $L_A/L_0 = 0.707$ $$\frac{DT_A/DT_S}{L_S/L_0} = 3.22$$

$|C| = 0.2862$, $|X_A - X_S| = 0.2441$ ($f = 1$)

EMBODIMENT 7

$f = 0.875$, $IH = 0.7725$, $2\omega = 100°$

| | | | |
|---|---|---|---|
| $r_1 = \infty$ | $d_1 = 0.2365$ | $n_1 = 1.51633$ | $\nu_1 = 64.15$ |

-continued

| | f = 0.875, IH = 0.7725, 2ω = 100° | | |
|---|---|---|---|
| $r_2 = \infty$ | $d_2 = 0.1577$ | | |
| $r_3 = \infty$ | $d_3 = 0.1577$ | $n_2 = 1.78800$ | $\nu_2 = 47.43$ |
| $r_4 = 0.5781$ | $d_4 = 0.2365$ | | |
| $r_5 = \infty$ | $d_5 = 0.6587$ | $n_3 = 1.78800$ | $\nu_3 = 47.43$ |
| $r_6 = \infty$ (stop) | $d_6 = 3.2828$ | $n_4 = 1.78800$ | $\nu_4 = 47.43$ |
| $r_7 = -1.7834$ | $d_7 = 0.0788$ | | |
| $r_8 = 3.8305$ | $d_8 = 1.3953$ | $n_5 = 1.63854$ | $\nu_5 = 55.38$ |
| $r_9 = -1.3401$ | $d_9 = 0.5518$ | $n_6 = 1.84666$ | $\nu_6 = 23.88$ |
| $r_{10} = -2.3263$ | $d_{10} = 0.0202$ | | |
| $r_{11} = -3.4179$ | $d_{11} = 0.5518$ | $n_7 = 1.72825$ | $\nu_7 = 28.46$ |
| (aspherical surface) | | | |
| $r_{12} = 4.7448$ | $d_{12} = 1.0957$ | $n_8 = 1.77250$ | $\nu_8 = 49.66$ |
| $r_{13} = 18.8989$ | $d_{13} = 3.1532$ | | |
| $r_{14} = 15.2419$ | $d_{14} = 18.9190$ | $n_9 = 1.62004$ | $\nu_9 = 36.25$ |
| $r_{15} = \infty$ | $d_{15} = 1.3322$ | | |
| $r_{16} = 12.1839$ | $d_{16} = 2.0890$ | $n_{10} = 1.65160$ | $\nu_{10} = 58.67$ |
| $r_{17} = -2.7527$ | $d_{17} = 1.0642$ | $n_{11} = 1.80610$ | $\nu_{11} = 40.95$ |
| $r_{18} = -6.1487$ | $d_{18} = 2.2151$ | | |
| $r_{19} = \infty$ | $d_{19} = 18.9190$ | $n_{12} = 1.62004$ | $\nu_{12} = 36.25$ |
| $r_{20} = -8.9668$ | $d_{20} = 3.1532$ | | |
| $r_{21} = 8.9668$ | $d_{21} = 18.9190$ | $n_{13} = 1.62004$ | $\nu_{13} = 36.25$ |
| $r_{22} = \infty$ | $d_{22} = 1.3322$ | | |
| $r_{23} = 12.1839$ | $d_{23} = 2.0890$ | $n_{14} = 1.65160$ | $\nu_{14} = 58.67$ |
| $r_{24} = -2.7527$ | $d_{24} = 1.0642$ | $n_{15} = 1.80610$ | $\nu_{15} = 40.95$ |
| $r_{25} = -6.1487$ | $d_{25} = 2.2151$ | | |
| $r_{26} = \infty$ | $d_{26} = 18.9190$ | $n_{16} = 1.62004$ | $\nu_{16} = 36.25$ |
| $r_{27} = -8.9668$ | $d_{27} = 3.1532$ | | |
| $r_{28} = 8.9668$ | $d_{28} = 18.9190$ | $n_{17} = 1.62004$ | $\nu_{17} = 36.25$ |
| $r_{29} = \infty$ | $d_{29} = 1.3322$ | | |
| $r_{30} = 12.1839$ | $d_{30} = 2.0890$ | $n_{18} = 1.65160$ | $\nu_{18} = 58.67$ |
| $r_{31} = -2.7527$ | $d_{31} = 1.0642$ | $n_{19} = 1.80610$ | $\nu_{19} = 40.95$ |
| $r_{32} = -6.1487$ | $d_{32} = 2.2151$ | | |
| $r_{33} = \infty$ | $d_{33} = 18.9190$ | $n_{20} = 1.62004$ | $\nu_{20} = 36.25$ |
| $r_{34} = -8.9668$ | $d_{34} = 3.1532$ | | |
| $r_{35} = 8.9668$ | $d_{35} = 18.9190$ | $n_{21} = 1.62004$ | $\nu_{21} = 36.25$ |
| $r_{36} = \infty$ | $d_{36} = 1.3322$ | | |
| $r_{37} = 12.1839$ | $d_{37} = 2.0890$ | $n_{22} = 1.65160$ | $\nu_{22} = 58.67$ |
| $r_{38} = -2.7527$ | $d_{38} = 1.0642$ | $n_{23} = 1.80610$ | $\nu_{23} = 40.95$ |
| $r_{39} = -6.1487$ | $d_{39} = 2.2151$ | | |
| $r_{40} = \infty$ | $d_{40} = 18.9190$ | $n_{24} = 1.62004$ | $\nu_{24} = 36.25$ |
| $r_{41} = -8.9668$ | $d_{41} = 3.1532$ | | |
| $r_{42} = 8.9668$ | $d_{42} = 18.9190$ | $n_{25} = 1.62004$ | $\nu_{25} = 36.25$ |
| $r_{43} = \infty$ | $d_{43} = 1.3322$ | | |
| $r_{44} = 12.1839$ | $d_{44} = 2.0890$ | $n_{26} = 1.65160$ | $\nu_{26} = 58.67$ |
| $r_{45} = -2.7527$ | $d_{45} = 1.0642$ | $n_{27} = 1.80610$ | $\nu_{27} = 40.95$ |
| $r_{46} = -6.1487$ | $d_{46} = 2.2151$ | | |
| $r_{47} = \infty$ | $d_{47} = 17.0902$ | $n_{28} = 1.62004$ | $\nu_{28} = 36.25$ |
| $r_{48} = \infty$ | $d_{48} = 1.7106$ | $n_{29} = 1.51633$ | $\nu_{29} = 64.15$ |
| $r_{49} = -19.8910$ | | | | aspherical surface coefficients
$E = -0.23539 \times 10^{-1}$
$F = -0.41655 \times 10^{-8}, G = 0.72219 \times 10^{-14}$
$DT = -25\%, L_A/L_0 = 0.678$ $$\frac{DT_A/DT_S}{L_S/L_0} = 5.1$$

$|C| = 0.256, |X_A - X_S| = 0.1655 \ (f = 1)$

EMBODIMENT 8

| | f = 0.76, IH = 0.7397, 2ω = 110° | | |
|---|---|---|---|
| $r_1 = \infty$ | $d_1 = 0.2265$ | $n_1 = 1.51633$ | $\nu_1 = 64.15$ |
| $r_2 = \infty$ | $d_2 = 0.1510$ | | |
| $r_3 = \infty$ | $d_3 = 0.1510$ | $n_2 = 1.78800$ | $\nu_2 = 47.43$ |
| $r_4 = 0.3665$ | $d_4 = 0.2265$ | | |
| $r_5 = \infty$ | $d_5 = 0.2085$ | $n_3 = 1.78800$ | $\nu_3 = 47.43$ |
| $r_6 = \infty$ (stop) | $d_6 = 3.5657$ | $n_4 = 1.78800$ | $\nu_4 = 47.43$ |
| $r_7 = -1.7664$ | $d_7 = 0.0755$ | | |
| $r_8 = 3.1657$ | $d_8 = 1.3361$ | $n_5 = 1.63854$ | $\nu_5 = 55.38$ |
| $r_9 = -1.2832$ | $d_9 = 0.5284$ | $n_6 = 1.84666$ | $\nu_6 = 23.88$ |
| $r_{10} = -2.2217$ | $d_{10} = 0.4437$ | | |
| $r_{11} = -1.6415$ | $d_{11} = 0.5284$ | $n_7 = 1.72825$ | $\nu_7 = 28.46$ |
| (aspherical surface) | | | |
| $r_{12} = 5.6173$ | $d_{12} = 1.0492$ | $n_8 = 1.77250$ | $\nu_8 = 49.66$ |
| $r_{13} = -23.3361$ | $d_{13} = 3.0194$ | | |
| $r_{14} = 16.3164$ | $d_{14} = 18.1161$ | $n_9 = 1.62004$ | $\nu_9 = 36.25$ |

-continued

| | f = 0.76, IH = 0.7397, 2ω = 110° | | |
|---|---|---|---|
| $r_{15} = \infty$ | $d_{15} = 1.2757$ | | |
| $r_{16} = 11.6668$ | $d_{16} = 2.0003$ | $n_{10} = 1.65160$ | $\nu_{10} = 58.67$ |
| $r_{17} = -2.6359$ | $d_{17} = 1.0190$ | $n_{11} = 1.80610$ | $\nu_{11} = 40.95$ |
| $r_{18} = -5.8877$ | $d_{18} = 2.1211$ | | |
| $r_{19} = \infty$ | $d_{19} = 18.1161$ | $n_{12} = 1.62004$ | $\nu_{12} = 36.25$ |
| $r_{20} = -8.5863$ | $d_{20} = 3.0194$ | | |
| $r_{21} = 8.5863$ | $d_{21} = 18.1161$ | $n_{13} = 1.62004$ | $\nu_{13} = 36.25$ |
| $r_{22} = \infty$ | $d_{22} = 1.2757$ | | |
| $r_{23} = 11.6668$ | $d_{23} = 2.0003$ | $n_{14} = 1.65160$ | $\nu_{14} = 58.67$ |
| $r_{24} = -2.6359$ | $d_{24} = 1.0190$ | $n_{15} = 1.80610$ | $\nu_{15} = 40.95$ |
| $r_{25} = -5.8877$ | $d_{25} = 2.1211$ | | |
| $r_{26} = \infty$ | $d_{26} = 18.1161$ | $n_{16} = 1.62004$ | $\nu_{16} = 36.25$ |
| $r_{27} = -8.5863$ | $d_{27} = 3.0194$ | | |
| $r_{28} = 8.5863$ | $d_{28} = 18.1161$ | $n_{17} = 1.62004$ | $\nu_{17} = 36.25$ |
| $r_{29} = \infty$ | $d_{29} = 1.2757$ | | |
| $r_{30} = 11.6668$ | $d_{30} = 2.0003$ | $n_{18} = 1.65160$ | $\nu_{18} = 58.67$ |
| $r_{31} = -2.6359$ | $d_{31} = 1.0190$ | $n_{19} = 1.80610$ | $\nu_{19} = 40.95$ |
| $r_{32} = -5.8877$ | $d_{32} = 2.1211$ | | |
| $r_{33} = \infty$ | $d_{33} = 18.1161$ | $n_{20} = 1.62004$ | $\nu_{20} = 36.25$ |
| $r_{34} = -8.5863$ | $d_{34} = 3.0194$ | | |
| $r_{35} = 8.5863$ | $d_{35} = 18.1161$ | $n_{21} = 1.62004$ | $\nu_{21} = 36.25$ |
| $r_{36} = \infty$ | $d_{36} = 1.2757$ | | |
| $r_{37} = 11.6668$ | $d_{37} = 2.0003$ | $n_{22} = 1.65160$ | $\nu_{22} = 58.67$ |
| $r_{38} = -2.6359$ | $d_{38} = 1.0190$ | $n_{23} = 1.80610$ | $\nu_{23} = 40.95$ |
| $r_{39} = -5.8877$ | $d_{39} = 2.1211$ | | |
| $r_{40} = \infty$ | $d_{40} = 18.1161$ | $n_{24} = 1.62004$ | $\nu_{24} = 36.25$ |
| $r_{41} = -8.5863$ | $d_{41} = 3.0194$ | | |
| $r_{42} = 8.5863$ | $d_{42} = 18.1161$ | $n_{25} = 1.62004$ | $\nu_{25} = 36.25$ |
| $r_{43} = \infty$ | $d_{43} = 1.2757$ | | |
| $r_{44} = 11.6668$ | $d_{44} = 2.0003$ | $n_{26} = 1.65160$ | $\nu_{26} = 58.67$ |
| $r_{45} = -2.6359$ | $d_{45} = 1.0190$ | $n_{27} = 1.80610$ | $\nu_{27} = 40.95$ |
| $r_{46} = -5.8877$ | $d_{46} = 2.1211$ | | |
| $r_{47} = \infty$ | $d_{47} = 16.3649$ | $n_{28} = 1.62004$ | $\nu_{28} = 36.25$ |
| $r_{48} = \infty$ | $d_{48} = 1.6380$ | $n_{29} = 1.51633$ | $\nu_{29} = 64.15$ |
| $r_{49} = -19.0469$ | | | | aspherical surface coefficients
$E = -0.13138 \times 10^{-1}$
$F = -0.17962 \times 10^{-7}, G = -0.24470 \times 10^{-13}$
$DT = -31\%, L_A/L_0 = 0.691$ $$\frac{DT_A/DT_S}{L_S/L_0} = 7.92$$

$|C| = 0.463, |X_A - X_S| = 0.0605 \ (f = 1)$

EMBODIMENT 9

| | f = 1.327, IH = 0.7281, 2ω = 60° | | |
|---|---|---|---|
| $r_1 = \infty$ | $d_1 = 0.2229$ | $n_1 = 1.51633$ | $\nu_1 = 64.15$ |
| $r_2 = \infty$ | $d_2 = 0.1486$ | | |
| $r_3 = \infty$ | $d_3 = 0.1486$ | $n_2 = 1.78800$ | $\nu_2 = 47.43$ |
| $r_4 = 0.4928$ | $d_4 = 0.2229$ | | |
| $r_5 = \infty$ | $d_5 = 0.6272$ | $n_3 = 1.78800$ | $\nu_3 = 47.43$ |
| $r_6 = \infty$ (stop) | $d_6 = 1.8617$ | $n_4 = 1.78800$ | $\nu_4 = 47.43$ |
| $r_7 = -1.8904$ | $d_7 = 0.2229$ | | |
| $r_8 = 3.6973$ | $d_8 = 1.4413$ | $n_5 = 1.64000$ | $\nu_5 = 60.09$ |
| $r_9 = -1.0904$ | $d_9 = 0.3715$ | $n_6 = 1.84666$ | $\nu_6 = 23.88$ |
| $r_{10} = -2.0668$ | $d_{10} = 1.3967$ | | |
| $r_{11} = -1.2392$ | $d_{11} = 0.3715$ | $n_7 = 1.72825$ | $\nu_7 = 28.46$ |
| $r_{12} = \infty$ | $d_{12} = 1.4785$ | $n_8 = 1.77250$ | $\nu_8 = 49.66$ |
| $r_{13} = -1.8872$ (aspherical surface) | $d_{13} = 2.9718$ | | |
| $r_{14} = 8.4510$ | $d_{14} = 17.8306$ | $n_9 = 1.62004$ | $\nu_9 = 36.25$ |
| $r_{15} = \infty$ | $d_{15} = 1.2556$ | | |
| $r_{16} = 11.4829$ | $d_{16} = 1.9688$ | $n_{10} = 1.65160$ | $\nu_{10} = 58.67$ |
| $r_{17} = -2.5944$ | $d_{17} = 1.0030$ | $n_{11} = 1.80610$ | $\nu_{11} = 40.95$ |
| $r_{18} = -5.7949$ | $d_{18} = 2.0877$ | | |
| $r_{19} = \infty$ | $d_{19} = 17.8306$ | $n_{12} = 1.62004$ | $\nu_{12} = 36.25$ |
| $r_{20} = 8.4510$ | $d_{20} = 2.9718$ | | |
| $r_{21} = 8.4510$ | $d_{21} = 17.8306$ | $n_{13} = 1.62004$ | $\nu_{13} = 36.25$ |
| $r_{22} = \infty$ | $d_{22} = 1.2556$ | | |
| $r_{23} = 11.4829$ | $d_{23} = 1.9688$ | $n_{14} = 1.65160$ | $\nu_{14} = 58.67$ |
| $r_{24} = -2.5944$ | $d_{24} = 1.0030$ | $n_{15} = 1.80610$ | $\nu_{15} = 40.95$ |
| $r_{25} = -5.7949$ | $d_{25} = 2.0877$ | | |
| $r_{26} = \infty$ | $d_{26} = 17.8306$ | $n_{16} = 1.62004$ | $\nu_{16} = 36.25$ |
| $r_{27} = -8.4510$ | $d_{27} = 2.9718$ | | |
| $r_{28} = 8.4510$ | $d_{28} = 17.8306$ | $n_{17} = 1.62004$ | $\nu_{17} = 36.25$ |

-continued

| | $f = 1.327$, IH $= 0.7281$, $2\omega = 60°$ | | |
|---|---|---|---|
| $r_{29} = \infty$ | $d_{29} = 1.2556$ | | |
| $r_{30} = 11.4829$ | $d_{30} = 1.9688$ | $n_{18} = 1.65160$ | $\nu_{18} = 58.67$ |
| $r_{31} = -2.5944$ | $d_{31} = 1.0030$ | $n_{19} = 1.80610$ | $\nu_{19} = 40.95$ |
| $r_{32} = -5.7949$ | $d_{32} = 2.0877$ | | |
| $r_{33} = \infty$ | $d_{33} = 17.8306$ | $n_{20} = 1.62004$ | $\nu_{20} = 36.25$ |
| $r_{34} = -8.4510$ | $d_{34} = 2.9718$ | | |
| $r_{35} = 8.4510$ | $d_{35} = 17.8306$ | $n_{21} = 1.62004$ | $\nu_{21} = 36.25$ |
| $r_{36} = \infty$ | $d_{36} = 1.2556$ | | |
| $r_{37} = 11.4829$ | $d_{37} = 1.9688$ | $n_{22} = 1.65160$ | $\nu_{22} = 58.67$ |
| $r_{38} = -2.5944$ | $d_{38} = 1.0030$ | $n_{23} = 1.80610$ | $\nu_{23} = 40.95$ |
| $r_{39} = -5.7949$ | $d_{39} = 2.0877$ | | |
| $r_{40} = \infty$ | $d_{40} = 17.8306$ | $n_{24} = 1.62004$ | $\nu_{24} = 36.25$ |
| $r_{41} = -8.4510$ | $d_{41} = 2.9718$ | | |
| $r_{42} = 8.4510$ | $d_{42} = 17.8306$ | $n_{25} = 1.62004$ | $\nu_{25} = 36.25$ |
| $r_{43} = \infty$ | $d_{43} = 1.2556$ | | |
| $r_{44} = 11.4829$ | $d_{44} = 1.9688$ | $n_{26} = 1.65160$ | $\nu_{26} = 58.67$ |
| $r_{45} = -2.5944$ | $d_{45} = 1.0030$ | $n_{27} = 1.80610$ | $\nu_{27} = 40.95$ |
| $r_{46} = -5.7949$ | $d_{46} = 2.0877$ | | |
| $r_{47} = \infty$ | $d_{47} = 16.1070$ | $n_{28} = 1.62004$ | $\nu_{28} = 36.25$ |
| $r_{48} = \infty$ | $d_{48} = 1.6122$ | $n_{29} = 1.51633$ | $\nu_{29} = 64.15$ |
| $r_{49} = -18.7467$ | | | | aspherical surface coefficients
$E = 0.48214 \times 10^{-1}$
$F = 0.48474 \times 10^{-2}$, $G = -0.18050 \times 10^{-1}$
$DT = -4.5\%$, $L_A/L_0 = 0.851$ $$\frac{DT_A/DT_S}{L_S/L_0} = 2.99$$

$|C| = 0.7032$, $|X_A - X_S| = 1.3472$ ($f = 1$)

EMBODIMENT 10

| | $f = 0.931$, IH $= 0.7728$, $2\omega = 86.4°$ | | |
|---|---|---|---|
| $r_1 = \infty$ | $d_1 = 0.2366$ | $n_1 = 1.51633$ | $\nu_1 = 64.15$ |
| $r_2 = \infty$ | $d_2 = 0.1577$ | | |
| $r_3 = \infty$ | $d_3 = 0.1577$ | $n_2 = 1.78800$ | $\nu_2 = 47.43$ |
| $r_4 = 0.6070$ | $d_4 = 0.2366$ | | |
| $r_5 = \infty$ | $d_5 = 0.2523$ | $n_3 = 1.88300$ | $\nu_3 = 40.78$ |
| $r_6 = \infty$ (stop) | $d_6 = 1.0806$ | $n_4 = 1.88300$ | $\nu_4 = 40.78$ |
| $r_7 = \infty$ | $d_7 = 0.6955$ | $n_5 = 1.78800$ | $\nu_5 = 47.43$ |
| $r_8 = -1.9474$ | $d_8 = 0.0789$ | | |
| $r_9 = 1.6949$ | $d_9 = 1.1119$ | $n_6 = 1.64000$ | $\nu_6 = 60.09$ |
| $r_{10} = -1.5080$ | $d_{10} = 0.8123$ | $n_7 = 1.84666$ | $\nu_7 = 23.88$ |
| $r_{11} = 2.1169$ | $d_{11} = 0.3645$ | | |
| $r_{12} = -3.0455$ | $d_{12} = 0.4653$ | $n_8 = 1.72825$ | $\nu_8 = 28.46$ |
| $r_{13} = -1.7408$ | $d_{13} = 0.8123$ | $n_9 = 1.77250$ | $\nu_9 = 49.66$ |
| $r_{14} = -1.3939$ | $d_{14} = 3.1545$ | | |
| (aspherical surface) | | | |
| $r_{15} = 8.6143$ | $d_{15} = 18.9267$ | $n_{10} = 1.62004$ | $\nu_{10} = 36.25$ |
| $r_{16} = \infty$ | $d_{16} = 1.3328$ | | |
| $r_{17} = 12.1888$ | $d_{17} = 2.0898$ | $n_{11} = 1.65160$ | $\nu_{11} = 58.67$ |
| $r_{18} = -2.7538$ | $d_{18} = 1.0646$ | $n_{12} = 1.80610$ | $\nu_{12} = 40.95$ |
| $r_{19} = -6.1512$ | $d_{19} = 2.2160$ | | |
| $r_{20} = \infty$ | $d_{20} = 18.9267$ | $n_{13} = 1.62004$ | $\nu_{13} = 36.25$ |
| $r_{21} = -8.9705$ | $d_{21} = 3.1545$ | | |
| $r_{22} = 8.9705$ | $d_{22} = 18.9267$ | $n_{14} = 1.62004$ | $\nu_{14} = 36.25$ |
| $r_{23} = \infty$ | $d_{23} = 1.3328$ | | |
| $r_{24} = 12.1888$ | $d_{24} = 2.0898$ | $n_{15} = 1.65160$ | $\nu_{15} = 58.67$ |
| $r_{25} = -2.7538$ | $d_{25} = 1.0646$ | $n_{16} = 1.80610$ | $\nu_{16} = 40.95$ |
| $r_{26} = -6.1512$ | $d_{26} = 2.2160$ | | |
| $r_{27} = \infty$ | $d_{27} = 18.9267$ | $n_{17} = 1.62004$ | $\nu_{17} = 36.25$ |
| $r_{28} = -8.9705$ | $d_{28} = 3.1545$ | | |
| $r_{29} = 8.9705$ | $d_{29} = 18.9267$ | $n_{18} = 1.62004$ | $\nu_{18} = 36.25$ |
| $r_{30} = \infty$ | $d_{30} = 1.3328$ | | |
| $r_{31} = 12.1888$ | $d_{31} = 2.0898$ | $n_{19} = 1.65160$ | $\nu_{19} = 58.67$ |
| $r_{32} = -2.7538$ | $d_{32} = 1.0646$ | $n_{20} = 1.80610$ | $\nu_{20} = 40.95$ |
| $r_{33} = -6.1512$ | $d_{33} = 2.2160$ | | |
| $r_{34} = \infty$ | $d_{34} = 18.9267$ | $n_{21} = 1.62004$ | $\nu_{21} = 36.25$ |
| $r_{35} = -8.9705$ | $d_{35} = 3.1545$ | | |
| $r_{36} = 8.9705$ | $d_{36} = 18.9267$ | $n_{22} = 1.62004$ | $\nu_{22} = 36.25$ |
| $r_{37} = \infty$ | $d_{37} = 1.3328$ | | |
| $r_{38} = 12.1888$ | $d_{38} = 2.0898$ | $n_{23} = 1.65160$ | $\nu_{23} = 58.67$ |
| $r_{39} = -2.7538$ | $d_{39} = 1.0646$ | $n_{24} = 1.80610$ | $\nu_{24} = 40.95$ |
| $r_{40} = -6.1512$ | $d_{40} = 2.2160$ | | |
| $r_{41} = \infty$ | $d_{41} = 18.9267$ | $n_{25} = 1.62004$ | $\nu_{25} = 36.25$ |
| $r_{42} = -8.9705$ | $d_{42} = 3.1545$ | | |

-continued $f = 0.931$, $IH = 0.7728$, $2\omega = 86.4°$

| | | | |
|---|---|---|---|
| $r_{43} = 8.9705$ | $d_{43} = 18.9267$ | $n_{26} = 1.62004$ | $\nu_{26} = 36.25$ |
| $r_{44} = \infty$ | $d_{44} = 1.3328$ | | |
| $r_{45} = 12.1888$ | $d_{45} = 2.0898$ | $n_{27} = 1.65160$ | $\nu_{27} = 58.67$ |
| $r_{46} = -2.7538$ | $d_{46} = 1.0646$ | $n_{28} = 1.80610$ | $\nu_{28} = 40.95$ |
| $r_{47} = -6.1512$ | $d_{47} = 2.2160$ | | |
| $r_{48} = \infty$ | $d_{48} = 17.0971$ | $n_{29} = 1.62004$ | $\nu_{29} = 36.25$ |
| $r_{49} = \infty$ | $d_{49} = 1.7113$ | $n_{30} = 1.51633$ | $\nu_{30} = 64.15$ |
| $r_{50} = -19.8991$ | | | | aspherical surface coefficients
$E = 0.12123$
$F = 0.13554 \times 10^{-2}$, $G = -0.61995 \times 10^{-2}$
$DT = -9.8\%$, $L_A/L_0 = 0.846$ $$\frac{DT_A/DT_S}{L_S/L_0} = 1.91$$

$|C| = 0.668$, $|X_A - X_S| = 0.3275$ $(f = 1)$

EMBODIMENT 11

$f = 0.821$, $IH = 0.7213$, $2\omega = 100°$

| | | | |
|---|---|---|---|
| $r_1 = \infty$ | $d_1 = 0.2208$ | $n_1 = 1.51633$ | $\nu_1 = 64.15$ |
| $r_2 = \infty$ | $d_2 = 0.1472$ | | |
| $r_3 = \infty$ | $d_3 = 0.1472$ | $n_2 = 1.78800$ | $\nu_2 = 47.43$ |
| $r_4 = 0.4823$ | $d_4 = 0.2208$ | | |
| $r_5 = \infty$ | $d_5 = 0.8254$ | $n_3 = 1.78800$ | $\nu_3 = 47.43$ |
| $r_6 = \infty$ (stop) | $d_6 = 2.9722$ | $n_4 = 1.78800$ | $\nu_4 = 47.43$ |
| $r_7 = -2.0219$ | $d_7 = 0.0736$ | | |
| $r_8 = 4.7913$ | $d_8 = 1.3027$ | $n_5 = 1.63854$ | $\nu_5 = 55.38$ |
| $r_9 = -1.2872$ | $d_9 = 0.5152$ | $n_6 = 1.84666$ | $\nu_6 = 23.88$ |
| $r_{10} = -2.3380$ | $d_{10} = 0.5648$ | | |
| $r_{11} = -4.9163$ | $d_{11} = 0.5152$ | $n_7 = 1.72825$ | $\nu_7 = 28.46$ |
| $r_{12} = 2.5517$ | $d_{12} = 1.0230$ | $n_8 = 1.77250$ | $\nu_8 = 49.66$ |
| $r_{13} = -14.3095$ | $d_{13} = 2.9439$ | | |
| (aspherical surface) | | | |
| $r_{14} = 5.3249$ | $d_{14} = 17.6634$ | $n_9 = 1.62004$ | $\nu_9 = 36.25$ |
| $r_{15} = \infty$ | $d_{15} = 1.2438$ | | |
| $r_{16} = 11.3752$ | $d_{16} = 1.9503$ | $n_{10} = 1.65160$ | $\nu_{10} = 58.67$ |
| $r_{17} = -2.5700$ | $d_{17} = 0.9936$ | $n_{11} = 1.80610$ | $\nu_{11} = 40.95$ |
| $r_{18} = -5.7406$ | $d_{18} = 2.0681$ | | |
| $r_{19} = \infty$ | $d_{19} = 17.6634$ | $n_{12} = 1.62004$ | $\nu_{12} = 36.25$ |
| $r_{20} = -8.3717$ | $d_{20} = 2.9439$ | | |
| $r_{21} = 8.3717$ | $d_{21} = 17.6634$ | $n_{13} = 1.62004$ | $\nu_{13} = 36.25$ |
| $r_{22} = \infty$ | $d_{22} = 1.2438$ | | |
| $r_{23} = 11.3752$ | $d_{23} = 1.9503$ | $n_{14} = 1.65160$ | $\nu_{14} = 58.67$ |
| $r_{24} = -2.5700$ | $d_{24} = 0.9936$ | $n_{15} = 1.80610$ | $\nu_{15} = 40.95$ |
| $r_{25} = -5.7406$ | $d_{25} = 2.0681$ | | |
| $r_{26} = \infty$ | $d_{26} = 17.6634$ | $n_{16} = 1.62004$ | $\nu_{16} = 36.25$ |
| $r_{27} = -8.3717$ | $d_{27} = 2.9439$ | | |
| $r_{28} = 8.3717$ | $d_{28} = 17.6634$ | $n_{17} = 1.62004$ | $\nu_{17} = 36.25$ |
| $r_{29} = \infty$ | $d_{29} = 1.2438$ | | |
| $r_{30} = 11.3752$ | $d_{30} = 1.9503$ | $n_{18} = 1.65160$ | $\nu_{18} = 58.67$ |
| $r_{31} = -2.5700$ | $d_{31} = 0.9936$ | $n_{19} = 1.80610$ | $\nu_{19} = 40.95$ |
| $r_{32} = -5.7406$ | $d_{32} = 2.0681$ | | |
| $r_{33} = \infty$ | $d_{33} = 17.6634$ | $n_{20} = 1.62004$ | $\nu_{20} = 36.25$ |
| $r_{34} = -8.3717$ | $d_{34} = 2.9439$ | | |
| $r_{35} = 8.3717$ | $d_{35} = 17.6634$ | $n_{21} = 1.62004$ | $\nu_{21} = 36.25$ |
| $r_{36} = \infty$ | $d_{36} = 1.2438$ | | |
| $r_{37} = 11.3752$ | $d_{37} = 1.9503$ | $n_{22} = 1.65160$ | $\nu_{22} = 58.67$ |
| $r_{38} = -2.5700$ | $d_{38} = 0.9936$ | $n_{23} = 1.80610$ | $\nu_{23} = 40.95$ |
| $r_{39} = -5.7406$ | $d_{39} = 2.0681$ | | |
| $r_{40} = \infty$ | $d_{40} = 17.6634$ | $n_{24} = 1.62004$ | $\nu_{24} = 36.25$ |
| $r_{41} = -8.3717$ | $d_{41} = 2.9439$ | | |
| $r_{42} = 8.3717$ | $d_{42} = 17.6634$ | $n_{25} = 1.62004$ | $\nu_{25} = 36.25$ |
| $r_{43} = \infty$ | $d_{43} = 1.2438$ | | |
| $r_{44} = 11.3752$ | $d_{44} = 1.9503$ | $n_{26} = 1.65160$ | $\nu_{26} = 58.67$ |
| $r_{45} = -2.5700$ | $d_{45} = 0.9936$ | $n_{27} = 1.80610$ | $\nu_{27} = 40.95$ |
| $r_{46} = -5.7406$ | $d_{46} = 2.0681$ | | |
| $r_{47} = \infty$ | $d_{47} = 15.9559$ | $n_{28} = 1.62004$ | $\nu_{28} = 36.25$ |
| $r_{48} = \infty$ | $d_{48} = 1.5971$ | $n_{29} = 1.51633$ | $\nu_{29} = 64.15$ |
| $r_{49} = -18.5709$ | | | | aspherical surface coefficients
$E = 0.68650 \times 10^{-1}$
$F = 0.22166 \times 10^{-6}$, $G = 0.49055 \times 10^{-12}$
$DT = -25\%$, $L_A/L_0 = 0.853$ -continued f = 0.821,  IH = 0.7213,  2ω = 100°

$$\frac{DT_A/DT_S}{L_S/L_0} = 4.74$$

$|C| = 0.0574,  |X_A - X_S| = 0.3988 \text{ (f = 1)}$

EMBODIMENT 12 f = 0.777,  IH = 0.7585,  2ω = 110°

| | | | |
|---|---|---|---|
| $r_1 = \infty$ | $d_1 = 0.2322$ | $n_1 = 1.51633$ | $\nu_1 = 64.15$ |
| $r_2 = \infty$ | $d_2 = 0.1548$ | | |
| $r_3 = \infty$ | $d_3 = 0.1548$ | $n_2 = 1.78800$ | $\nu_2 = 47.43$ |
| $r_4 = 0.7213$ | $d_4 = 0.2322$ | | |
| $r_5 = \infty$ | $d_5 = 1.6335$ | $n_3 = 1.78800$ | $\nu_3 = 47.43$ |
| $r_6 = \infty$ (stop) | $d_6 = 2.3604$ | $n_4 = 1.78800$ | $\nu_4 = 47.43$ |
| $r_7 = -4.1084$ | $d_7 = 0.0774$ | | |
| $r_8 = 2.1253$ | $d_8 = 1.3699$ | $n_5 = 1.63854$ | $\nu_5 = 55.38$ |
| $r_9 = -1.3537$ | $d_9 = 0.5418$ | $n_6 = 1.84666$ | $\nu_6 = 23.88$ |
| $r_{10} = -4.0287$ | $d_{10} = 0.0774$ | | |
| $r_{11} = 16.5772$ | $d_{11} = 0.5418$ | $n_7 = 1.72825$ | $\nu_7 = 28.46$ |
| $r_{12} = 6.3663$ | $d_{12} = 1.0758$ | $n_8 = 1.77250$ | $\nu_8 = 49.66$ |
| $r_{13} = -5.2788$ | $d_{13} = 3.0959$ | | |
| (aspherical surface) | | | |
| $r_{14} = 12.6161$ | $d_{14} = 18.5756$ | $n_9 = 1.62004$ | $\nu_9 = 36.25$ |
| $r_{15} = \infty$ | $d_{15} = 1.3080$ | | |
| $r_{16} = 11.9627$ | $d_{16} = 2.0511$ | $n_{10} = 1.65160$ | $\nu_{10} = 58.67$ |
| $r_{17} = -2.7027$ | $d_{17} = 1.0449$ | $n_{11} = 1.80610$ | $\nu_{11} = 40.95$ |
| $r_{18} = -6.0371$ | $d_{18} = 2.1749$ | | |
| $r_{19} = \infty$ | $d_{19} = 18.5756$ | $n_{12} = 1.62004$ | $\nu_{12} = 36.25$ |
| $r_{20} = -8.8040$ | $d_{20} = 3.0959$ | | |
| $r_{21} = 8.8040$ | $d_{21} = 18.5756$ | $n_{13} = 1.62004$ | $\nu_{13} = 36.25$ |
| $r_{22} = \infty$ | $d_{22} = 1.3080$ | | |
| $r_{23} = 11.9627$ | $d_{23} = 2.0511$ | $n_{14} = 1.65160$ | $\nu_{14} = 58.67$ |
| $r_{24} = -2.7027$ | $d_{24} = 1.0449$ | $n_{15} = 1.80610$ | $\nu_{15} = 40.95$ |
| $r_{25} = -6.0371$ | $d_{25} = 2.1749$ | | |
| $r_{26} = \infty$ | $d_{26} = 18.5756$ | $n_{16} = 1.62004$ | $\nu_{16} = 36.25$ |
| $r_{27} = -8.8040$ | $d_{27} = 3.0959$ | | |
| $r_{28} = 8.8040$ | $d_{28} = 18.5756$ | $n_{17} = 1.62004$ | $\nu_{17} = 36.25$ |
| $r_{29} = \infty$ | $d_{29} = 1.3080$ | | |
| $r_{30} = 11.9627$ | $d_{30} = 2.0511$ | $n_{18} = 1.65160$ | $\nu_{18} = 58.67$ |
| $r_{31} = -2.7027$ | $d_{31} = 1.0449$ | $n_{19} = 1.80610$ | $\nu_{19} = 40.95$ |
| $r_{32} = -6.0371$ | $d_{32} = 2.1749$ | | |
| $r_{33} = \infty$ | $d_{33} = 18.5756$ | $n_{20} = 1.62004$ | $\nu_{20} = 36.25$ |
| $r_{34} = -8.8040$ | $d_{34} = 3.0959$ | | |
| $r_{35} = 8.8040$ | $d_{35} = 18.5756$ | $n_{21} = 1.62004$ | $\nu_{21} = 36.25$ |
| $r_{36} = \infty$ | $d_{36} = 1.3080$ | | |
| $r_{37} = 11.9627$ | $d_{37} = 2.0511$ | $n_{22} = 1.65160$ | $\nu_{22} = 58.67$ |
| $r_{38} = -2.7027$ | $d_{38} = 1.0449$ | $n_{23} = 1.80610$ | $\nu_{23} = 40.95$ |
| $r_{39} = -6.0371$ | $d_{39} = 2.1749$ | | |
| $r_{40} = \infty$ | $d_{40} = 18.5756$ | $n_{24} = 1.62004$ | $\nu_{24} = 36.25$ |
| $r_{41} = -8.8040$ | $d_{41} = 3.0959$ | | |
| $r_{42} = 8.8040$ | $d_{42} = 18.5756$ | $n_{25} = 1.62004$ | $\nu_{25} = 36.25$ |
| $r_{43} = \infty$ | $d_{43} = 1.3080$ | | |
| $r_{44} = 11.9627$ | $d_{44} = 2.0511$ | $n_{26} = 1.65160$ | $\nu_{26} = 58.67$ |
| $r_{45} = -2.7027$ | $d_{45} = 1.0449$ | $n_{27} = 1.80610$ | $\nu_{27} = 40.95$ |
| $r_{46} = -6.0371$ | $d_{46} = 2.1749$ | | |
| $r_{47} = \infty$ | $d_{47} = 16.7799$ | $n_{28} = 1.62004$ | $\nu_{28} = 36.25$ |
| $r_{48} = \infty$ | $d_{48} = 1.6795$ | $n_{29} = 1.51633$ | $\nu_{29} = 64.15$ |
| $r_{49} = -19.5299$ | | | | aspherical surface coefficients
E = 0.75715 × 10⁻¹
$F = 0.11253 \times 10^{-6}, G = 0.28302 \times 10^{-12}$
DT = -30%, $L_A/L_0 = 0.845$ $$\frac{DT_A/DT_S}{L_S/L_0} = 3.03$$

$|C| = 0.147,  |X_A - X_S| = 0.3717 \text{ (f = 1)}$ wherein the reference symbols $r_1, r_2, \ldots$ represent the radii of curvature on the surfaces of the respective lens elements, the reference symbols $d_1, d_2, \ldots$ designate the thicknesses of the respective lens elements and the airspaces reserved therebetween, the reference symbols $n_1, n_2, \ldots$ denote the refractive indices of the respective lens elements, and the reference symbols $\nu_1, \nu_2, \ldots$ represent the Abbe's numbers of the respective lens elements.

Figure 7:
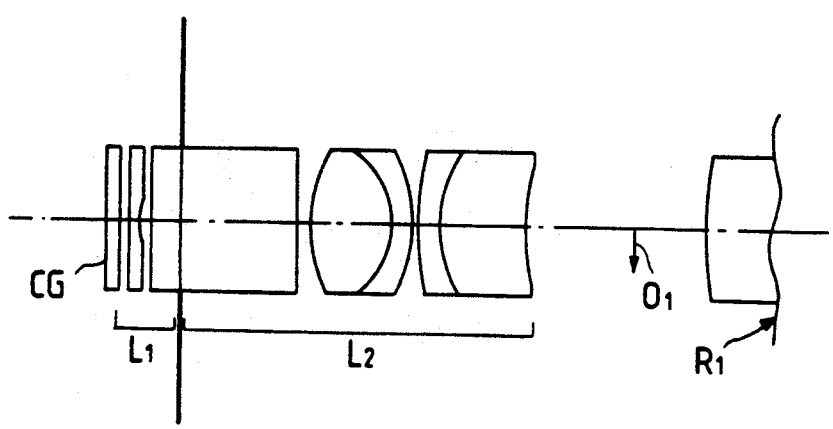
FIG. 7 shows a sectional view illustrating composition of an objective lens system which is to be used in Embodiment 1 of the optical system for endoscopes according to the present invention.
Figure 8:
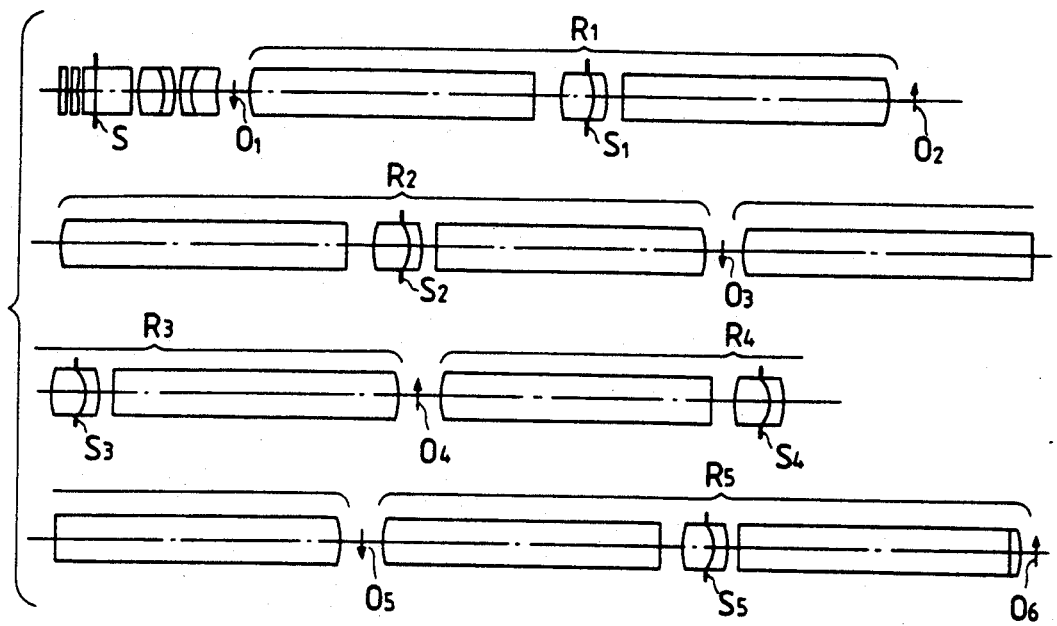
FIG. 8 shows a sectional view illustrating composition of the optical system for endoscopes according to the present invention.
Figure 9A:
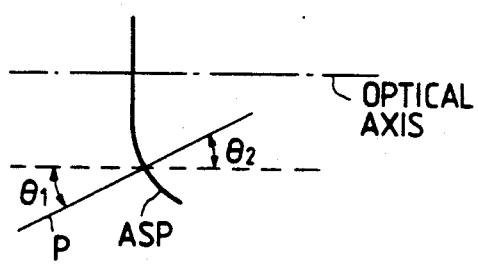
FIG. 9A and FIG. 9B show diagrams illustrating relationship between angle of incidence and angle of emergence of a principal ray on and from aspherical surfaces.
Figure 9B:
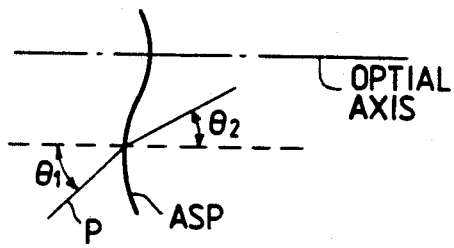
Figure 10A:
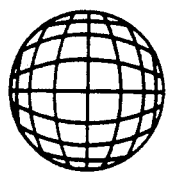
FIG. 10A, FIG. 10B, FIG. 10C and FIG. 10D show diagrams illustrating conditions of distortion produced by aspherical surfaces.
Figure 10B:
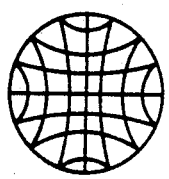
Figure 10C:
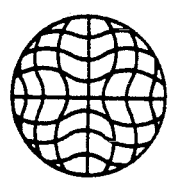
Figure 10D:
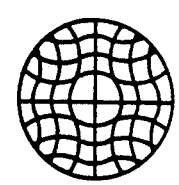
Figure 11A:
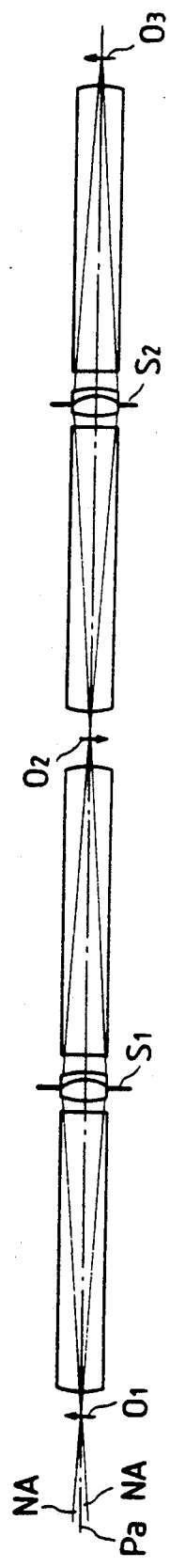
FIGS. 11A, 11B and 11C show sectional views descriptive of brightness of images transmitted by relay lens systems.
Figure 11B:
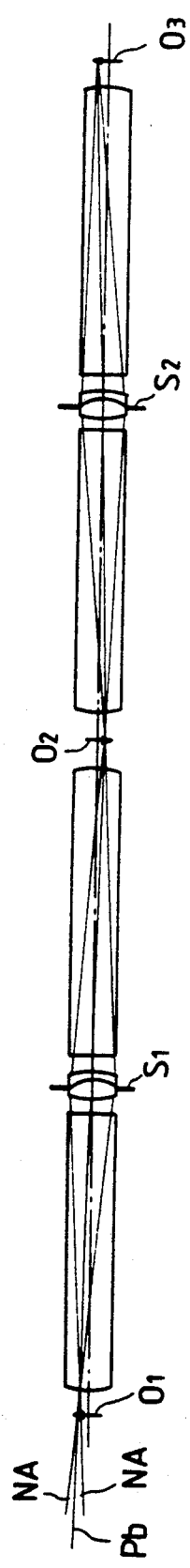
Figure 11C:
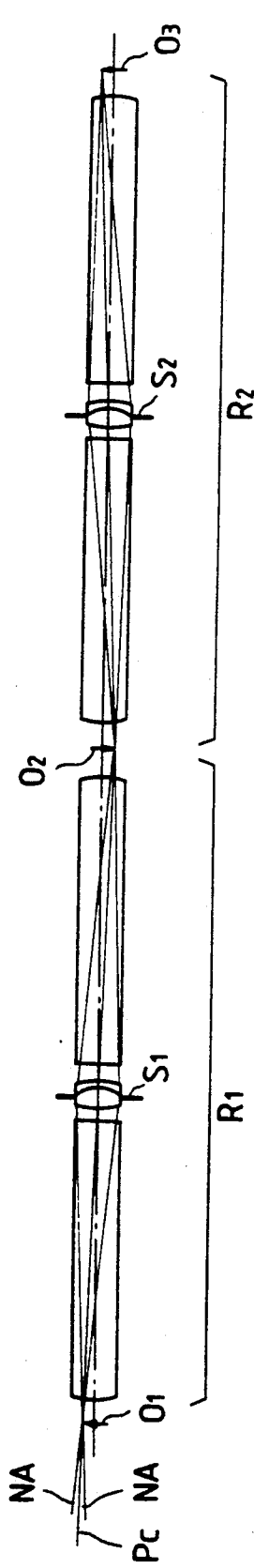
Figure 12A:
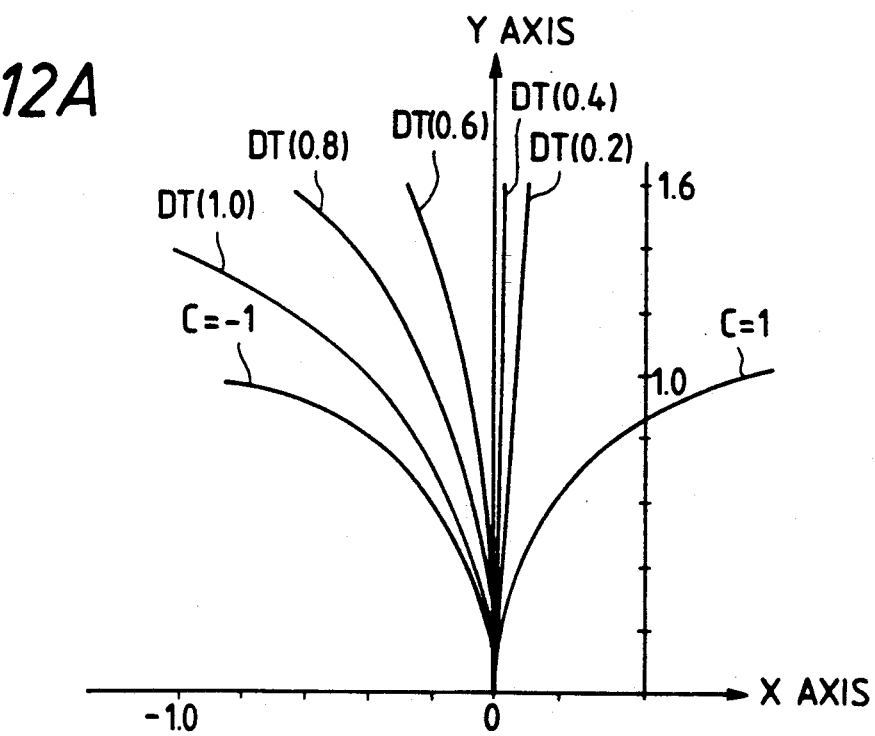
FIG. 12A and FIG. 12B show graphs illustrating relationship between shapes of aspherical surface and distortion.
Figure 12B:
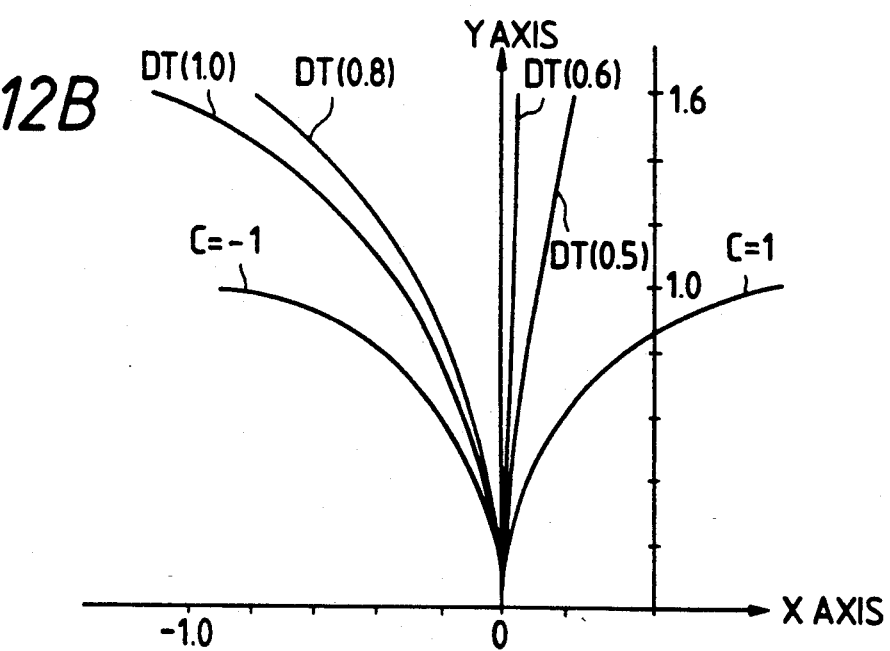

Each of the embodiments described above has the fundamental composition illustrated in FIG. 7 and FIG. 8 wherein the optical system for endoscopes according to the present invention comprises an objective lens system consisting of a first lens unit $L_1$ having a negative refractive power and a second lens unit $L_2$ having a positive refractive power, and relay lens systems $R_1$ through $R_5$, said second lens unit $L_2$ comprising at least one aspherical surface.

Out of these embodiments, the Embodiment 1 uses an objective lens system which has the composition illustrated in FIG. 7, is designed for a visual field angle of $2\omega=60°$ and uses an aspherical surface as the tenth surface ($r_{10}$). Further, this objective lens system has distortion DT of $-2\%$.

Figure 13:
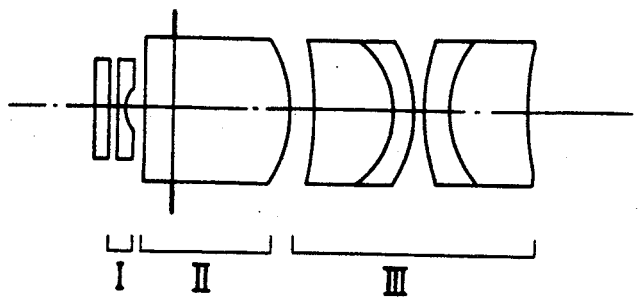
FIG. 13 through FIG. 18 show sectional views illustrating compositions of objective lens systems used in other embodiments of the optical system for endoscopes according to the present invention.

The objective lens systems used in the Embodiments 2 and 5 have the composition illustrated in FIG. 13. Out of these objective lens systems, the objective lens system used in the Embodiment 2 adopts an aspherical surface as the tenth surface ($r_{10}$), and has a visual field angle of $2\omega=4°$ and distortion of $DT=-15\%$, whereas the objective lens system adopted in the Embodiment 5 uses an aspherical surfaces as the eleventh surface ($r_{11}$), and has a visual field angle of $2\omega=60°$ and distortion of $DT=-2\%$.

Figure 14:
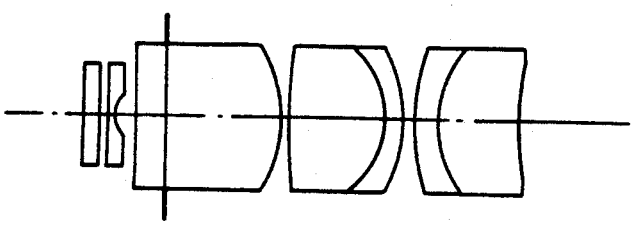

The objective lens systems used for the Embodiments 3, 6 and 12 have the composition illustrated in FIG. 14. In the Embodiment 3, the tenth surface ($r_{10}$) is designed as an aspherical surface, and the objective lens system has a field angle of $2\omega=100°$ and distortion of $DT=-25\%$. In the Embodiment 6, the fifth surface ($r_{15}$) is designed as an aspherical surface, and the objective lens system has a field angle of $2\omega=86.4°$ and distortion of $DT=-12\%$. The objective lens system used in the Embodiment 12 uses an aspherical surface as the thirteenth surface ($r_{13}$), and has a field angle of $2\omega=110°$ and distortion of $DT=-30\%$.

Figure 15:
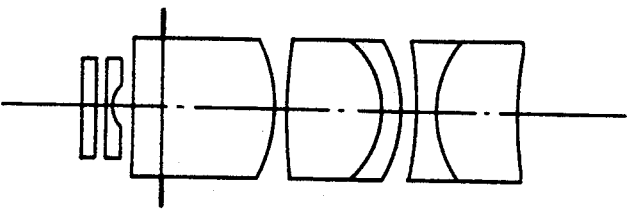

The objective lens systems adopted for the Embodiments 4 and 7 have the composition illustrated in FIG. 15. The objective lens system adopted in the Embodiment 4 uses an aspherical surface as the tenth surface ($r_{10}$), and has a field angle of $2\omega=110°$ and distortion of $DT=-32\%$. The objective lens system adopted for the Embodiment 7 uses an aspherical surface as the eleventh surface ($r_{11}$), and has a field angle of $2\omega=100°$ and distortion of $DT=-25\%$.

Figure 16:
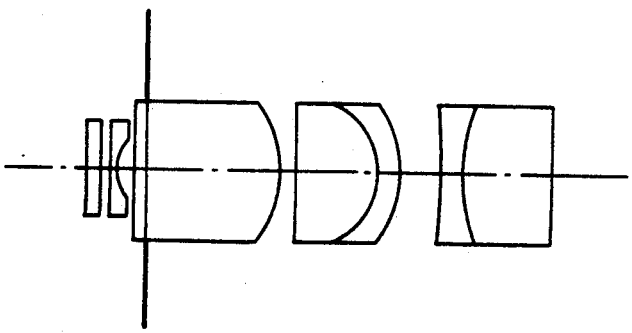

The objective lens systems selected for the Embodiments 8 and 11 have the composition shown in FIG. 16. The objective lens system adopted in the Embodiment 8 uses an aspherical surface as the eleventh surface ($r_{11}$), and is designed for $2\omega=110°$ and $DT=-31\%$. The objective lens system adopted in the Embodiment 11 uses an aspherical surface as the thirteenth surface ($r_{13}$), and has $2\omega=100°$ and $DT=-25\%$.

Figure 17:
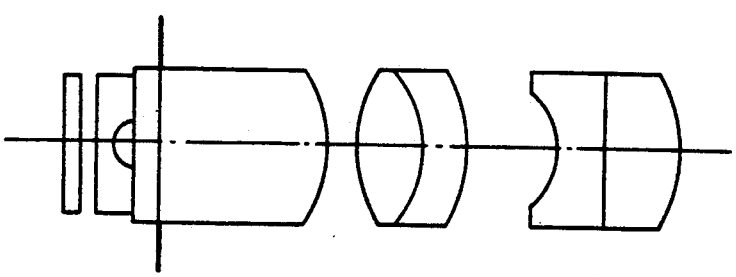

The objective lens system arranged in the Embodiment 9 has the composition illustrated in FIG. 17, uses an aspherical surface as the thirteenth surface ($r_{13}$), and has $2\omega=60°$ and $DT=-4.5\%$.

Figure 18:
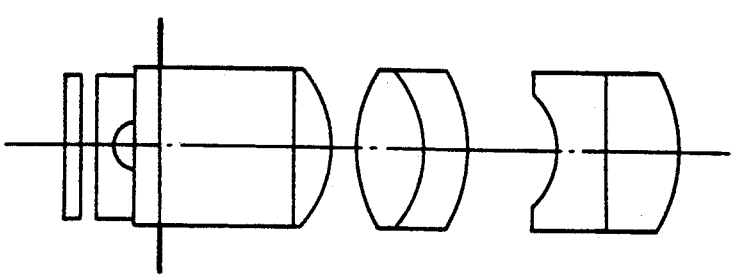
Figure 19:
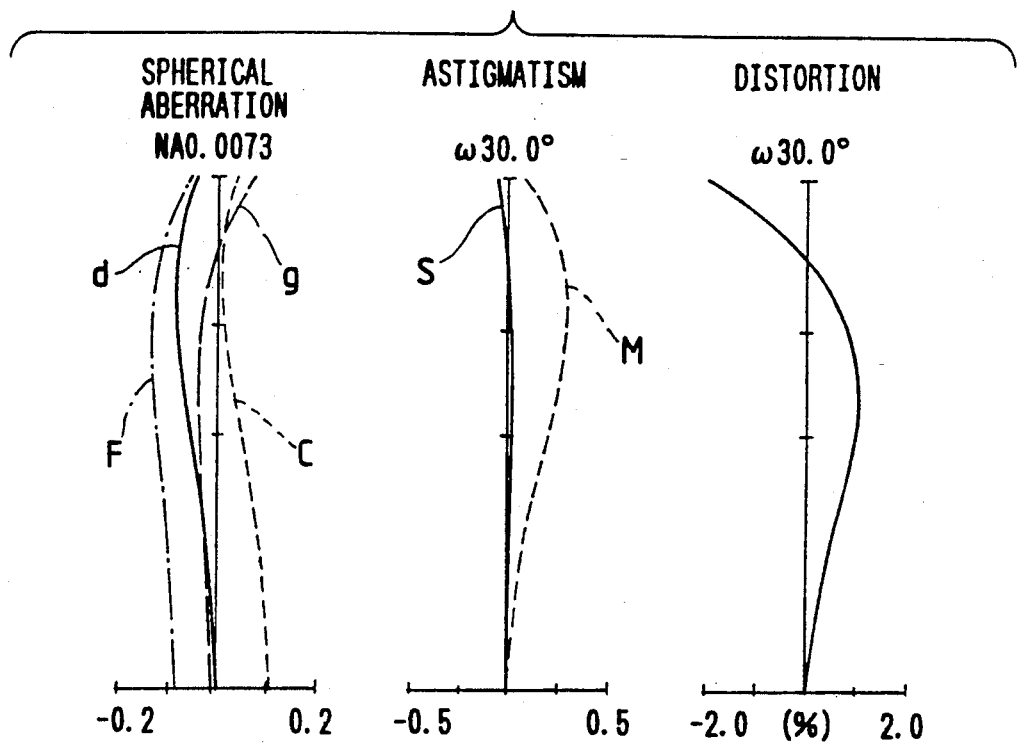
FIG. 19 through FIG. 30 show graphs illustrating aberration characteristics of the Embodiments 1 through 12 respectively of the optical system for endoscopes according to the present invention.
Figure 20:
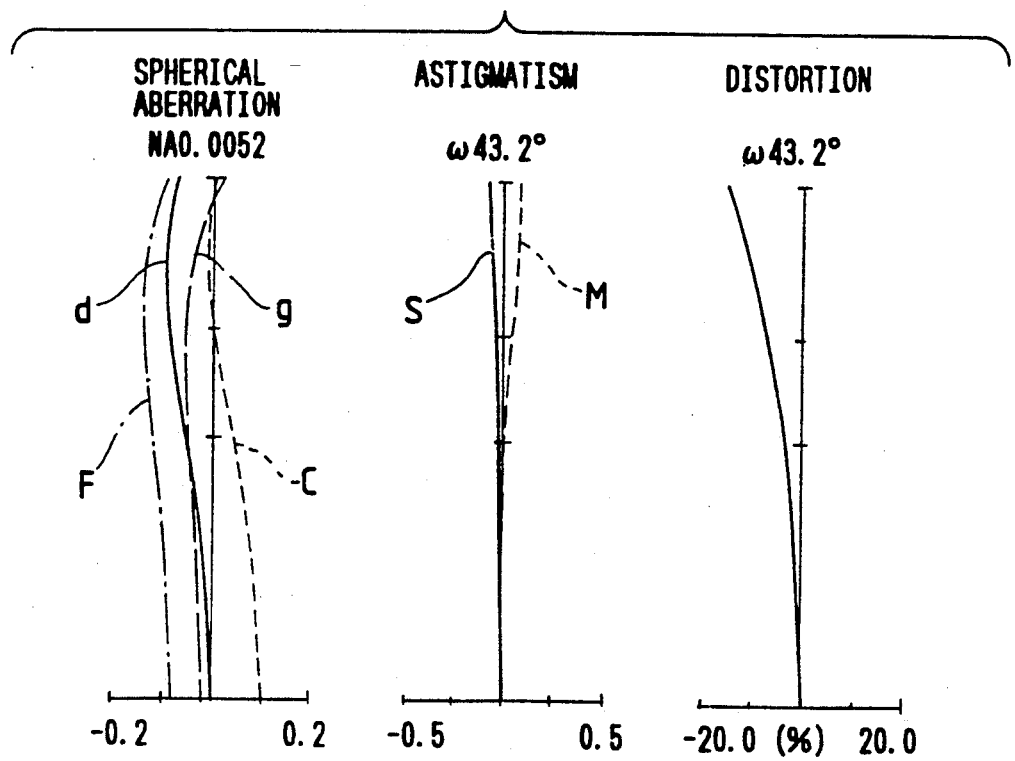
Figure 21:
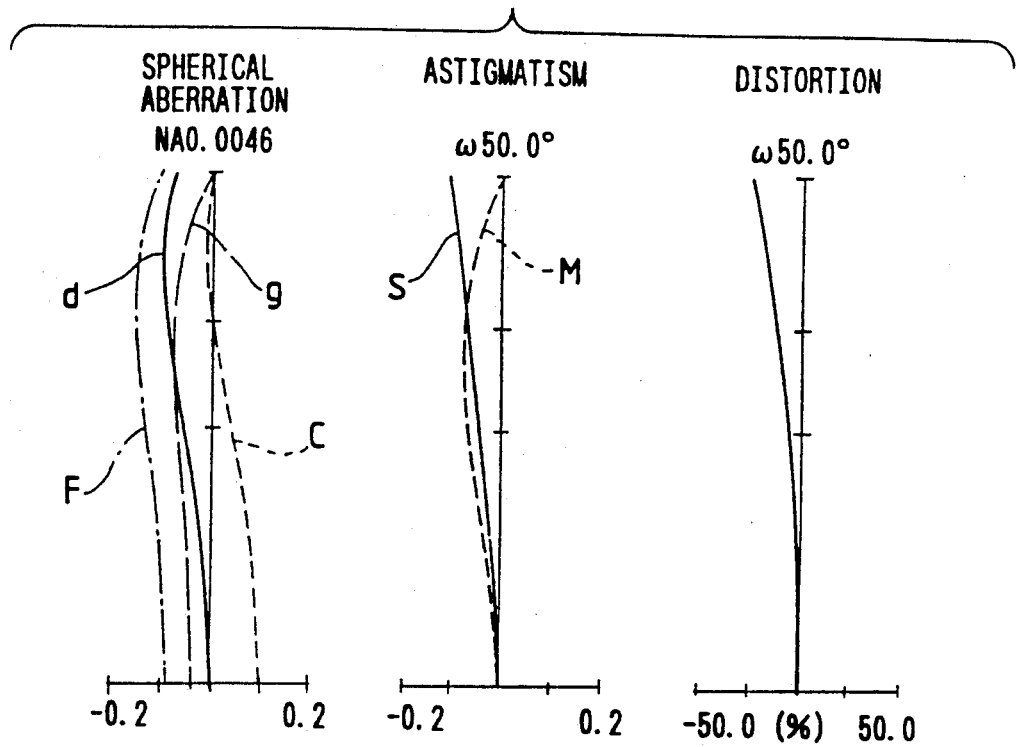
Figure 22:
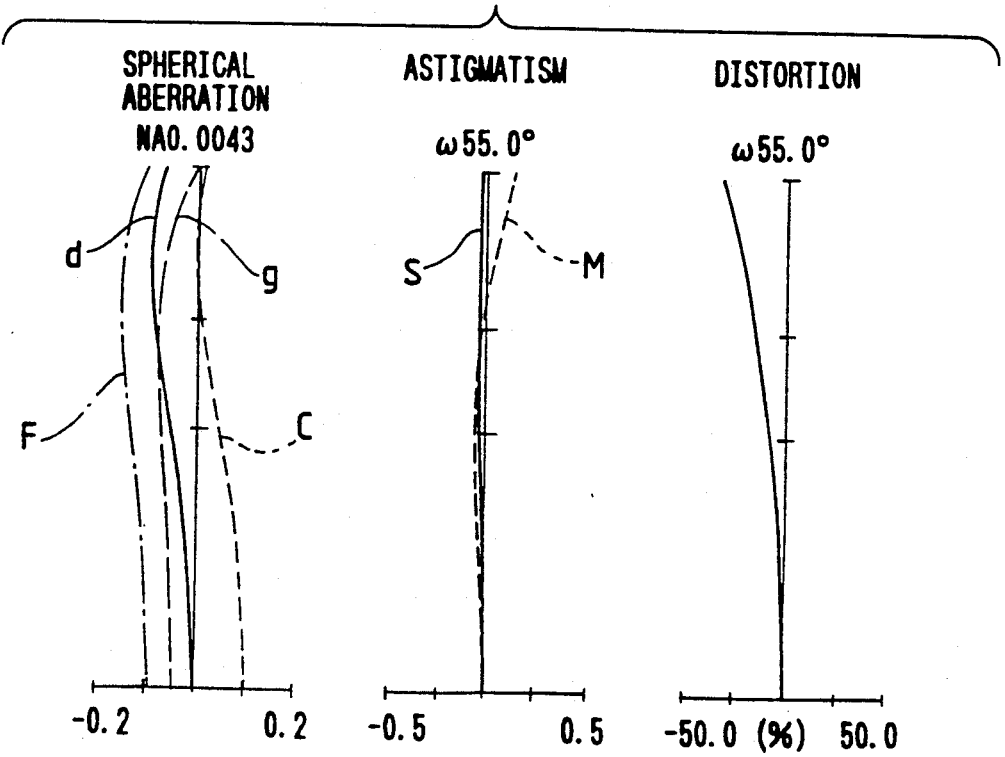
Figure 23:
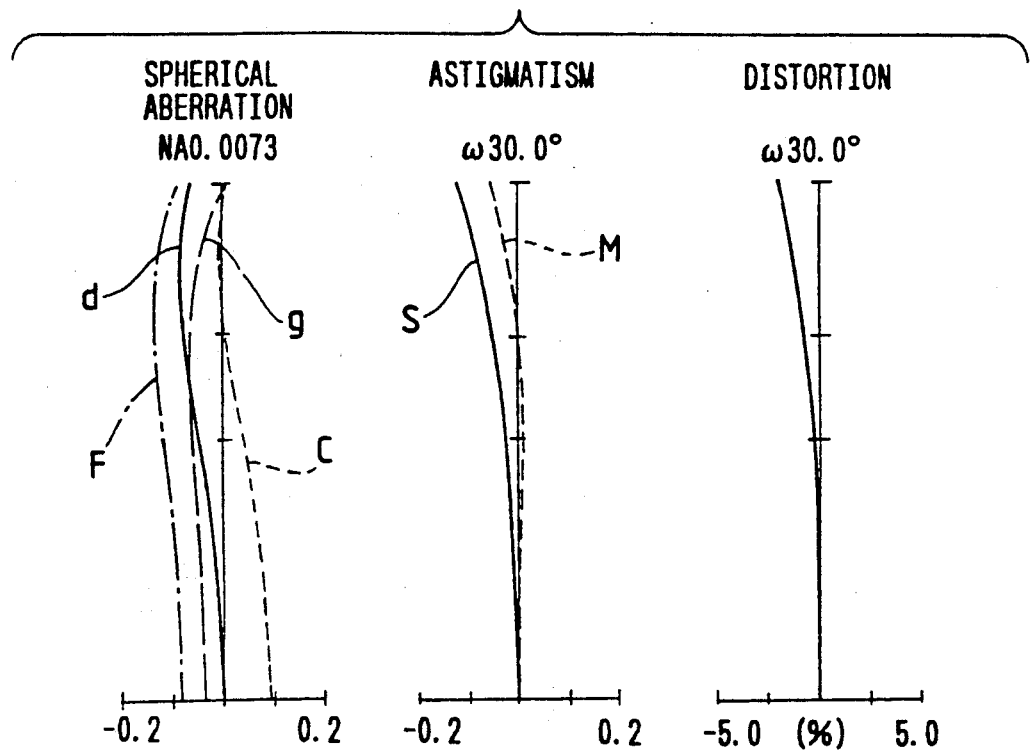
Figure 24:
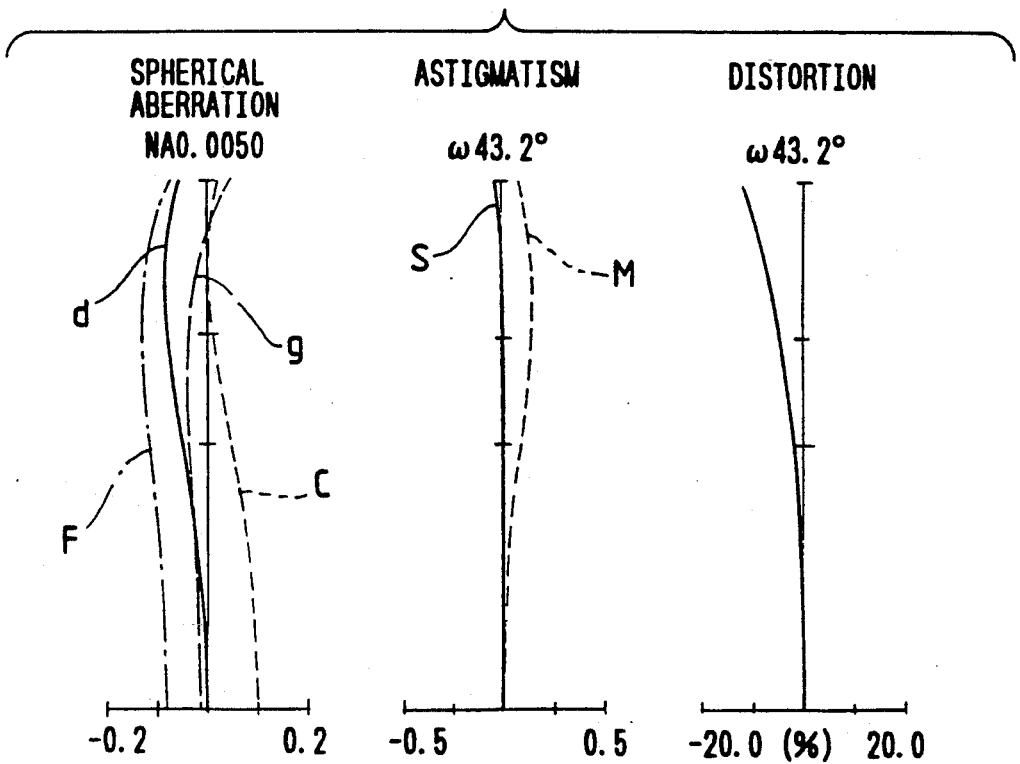
Figure 25:
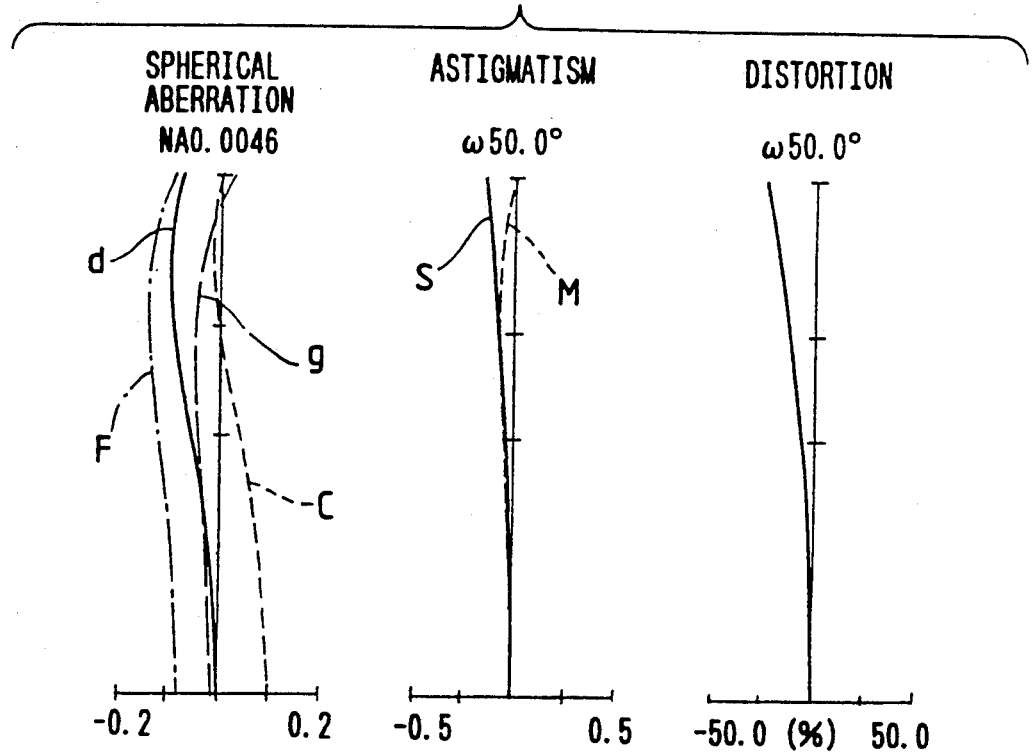
Figure 26:
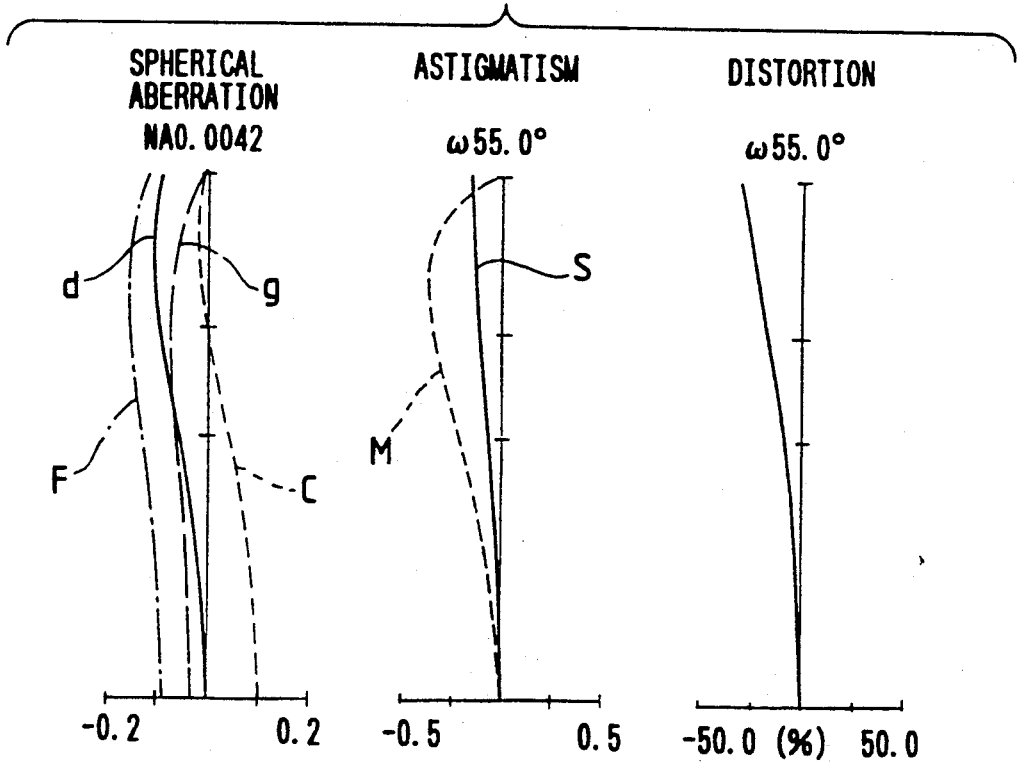
Figure 27:
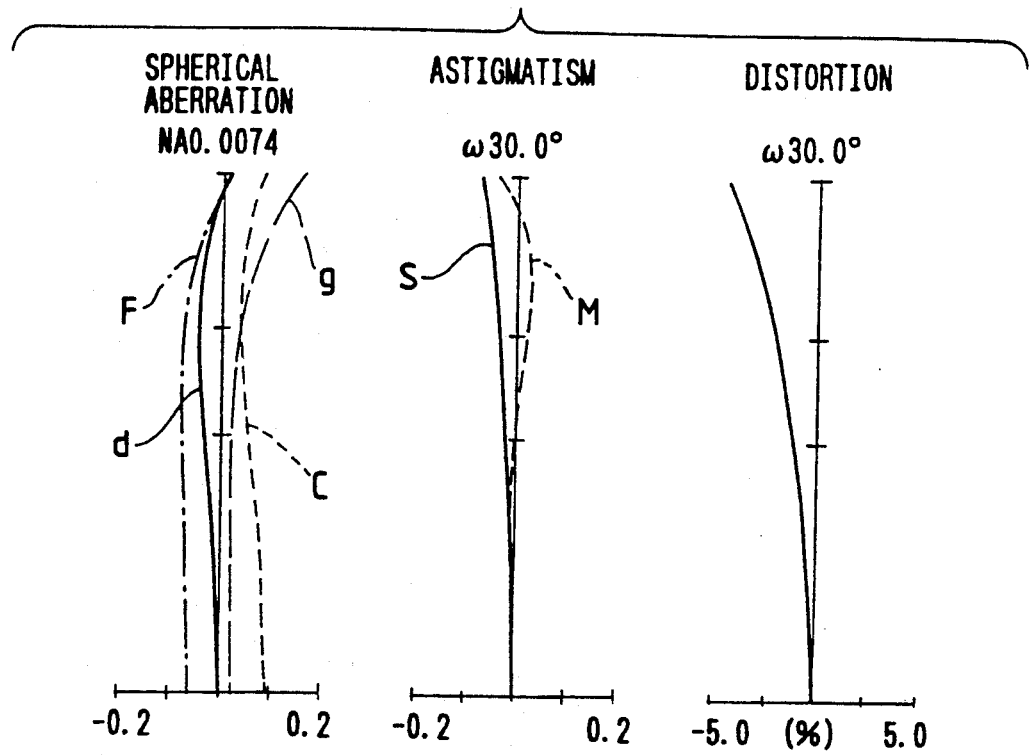
Figure 28:
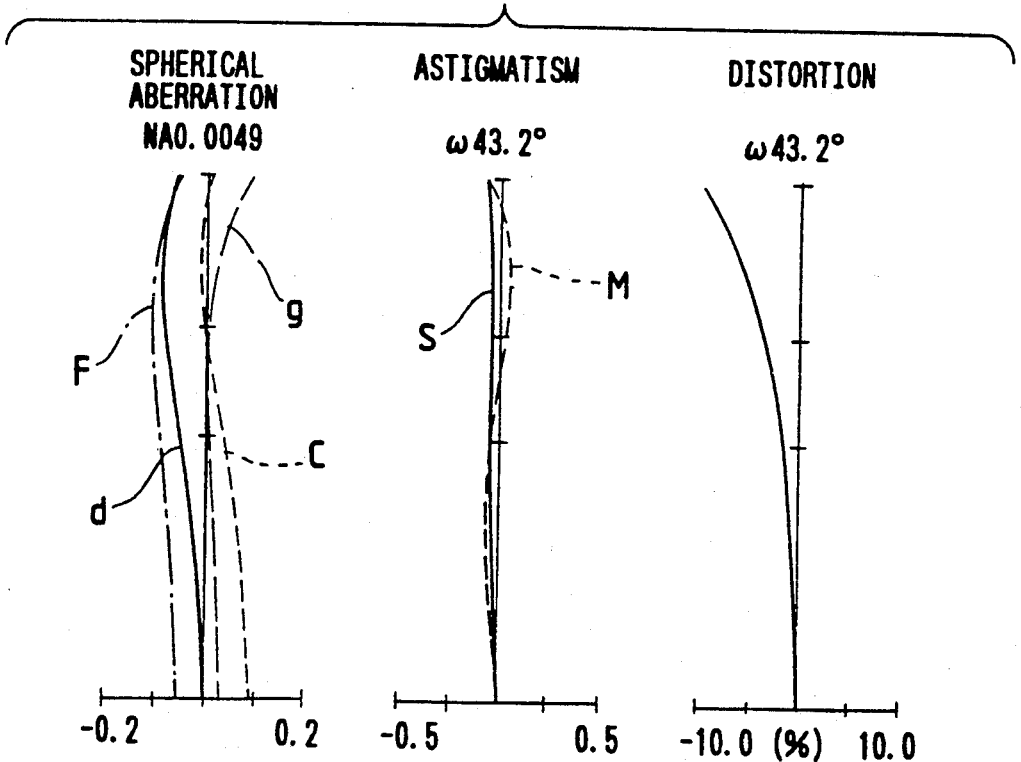
Figure 29:
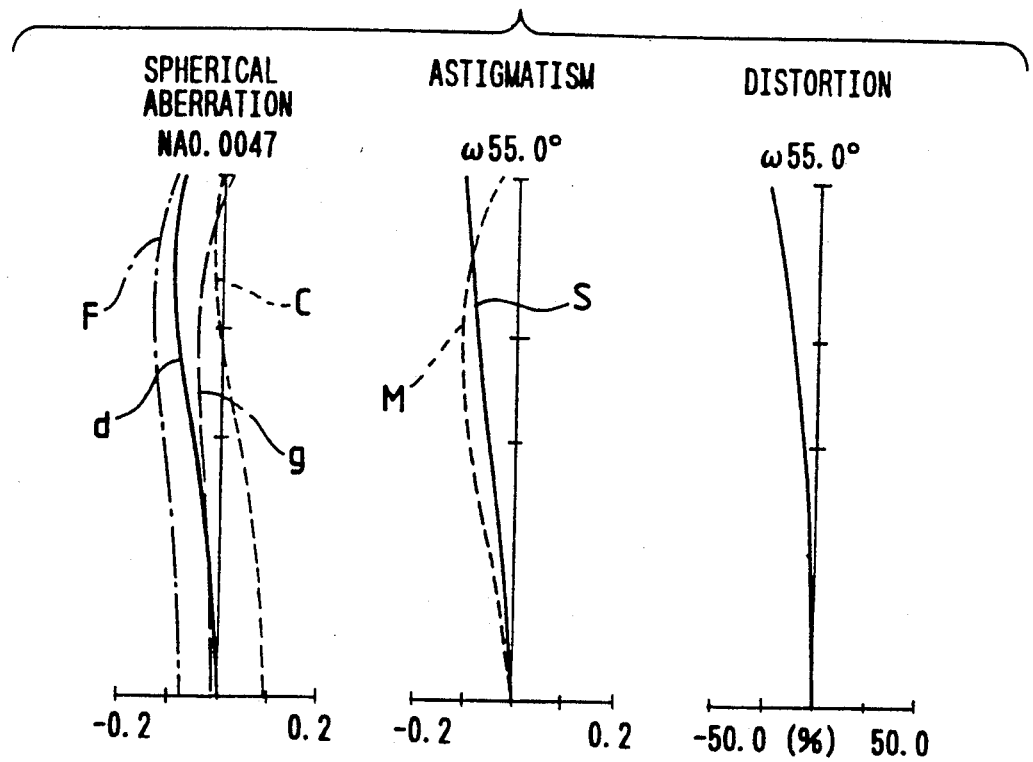
Figure 30:
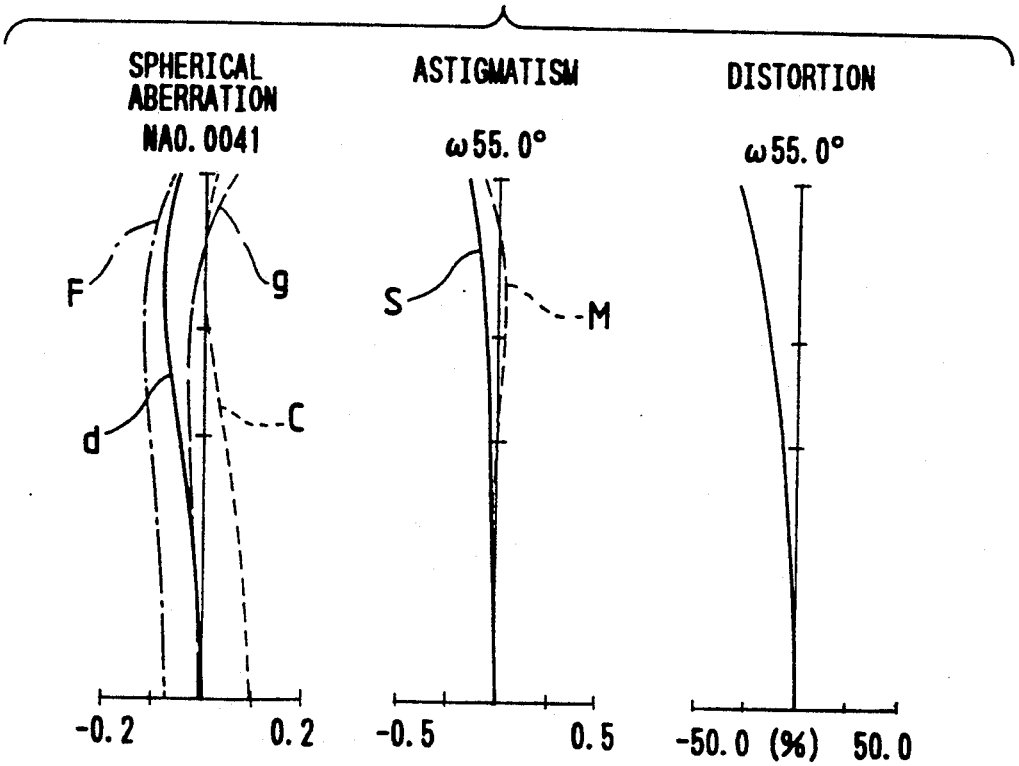

In the Embodiment 10, the objective lens system has the composition shown in FIG. 18. This objective lens system uses an aspherical surface as the fourteenth surface ($r_{14}$), and has $2\omega=60°$ and $DT=-9.8\%$.

As is clarified by the foregoing description, the embodiments of the optical system for endoscopes according to the present invention uses objective lens systems which are different in the visual field angle and distortion. The optical system for endoscopes according to the present invention has an advantage to permit adequately selecting visual field angle dependently on purposes of application, such as industrial inspections and medical diagnoses, and amounts of distortion dependently on shapes of objects to be observed.

When it is considered that the objective lens system used in each of the Embodiments 1 through 12 is divided into lens unit I, lens unit II and lens unit III, for example, as shown in FIG. 13, the lens unit I has a negative refractive power, the second lens unit II has a positive refractive power and lens unit III has a positive or negative refractive power.

The optical systems for endoscopes preferred as the Embodiments described above are designed on an assumption that they are to have outside diameters of 1.2 mm to 1.8 mm. Further, though each of the embodiments comprises five relay lens systems for erecting an inverted image formed by the objective lens system, it is possible to use even numbers of relay lens systems, a larger number of relay lens systems or a smaller number or relay lens systems dependently on purpose of application. Furthermore, it is possible to use graded refractive index lens elements in the relay lens systems.

As is understood from the foregoing description, the optical system for endoscopes according to the present invention is capable of correcting distortion which is abruptly aggravated as the field angle thereof is widened, assures brightness uniform over the entire range of an image from the center to the marginal portion thereof, nevertheless has an outside diameter within the restriction imposed on outside diameters of the optical systems for endoscopes and uses an aspherical surface which can easily be formed in practice.

I claim:

1. An optical system for an endoscope comprising, in the order from the object side;

an objective lens system comprising a first lens unit having a negative refractive power, a second lens unit having a positive refractive power and at least one aspherical surface arranged therein; and a relay lens system arranged on an image side of said objective lens system;

wherein said objective lens system satisfies condition (1):

$$0.3 < L_A/L_0 \qquad (1)$$

where:

$L_A$ represents a distance as measured along an optical axis from a first surface of said objective lens system to said aspherical surface; and $L_0$ designates a distance as measured along an optical axis from said first surface of said objective lens system to an image formed by said objective lens system.

2. An optical system for an endoscope according to claim 1, wherein said system also satisfies condition (2):

$$(2) \quad 0.1 < \frac{DT_A/DT_S}{L_S/L_0}$$

where $DT_A$ represents distortion at a maximum height of an image formed by said objective lens system;

$DT_S$ designates a value equal to $\cos\omega - 1$ where a visual field angle at the maximum image height is denoted by $\omega$; and $L_S$ represents a distance as measured along an optical axis from the first surface of said objective lens system to an imaginary aperture stop located in said objective lens system.

3. An optical system for an endoscope according to claim 2, wherein:
said aspherical surface has a shape defined by the equality shown below and satisfying condition (3):

$$x = \frac{Cy^2}{1 + \sqrt{1 - C^2 y^2}} + Ey^4 + Fy^6 + Gy^8 + \ldots$$

(3) $|C| < 1$ where x and y represent values on a coordinate system established by taking the optical axis as the abscissa, an intersection between the aspherical surface and the optical axis as the origin and a direction perpendicular to the optical axis as the ordinate;

C designates an inverse of a radius of curvature on a reference sphere of the aspherical surface; and E, F, G, ... denote coefficients of the aspherical surface of the fourth, sixth, eighth, ... orders, respectively.

4. An optical system for an endoscope according to claim 3, wherein:
said aspherical surface satisfies condition (4):

$$|X_A - X_S| < 1.5 \qquad (4)$$

where $X_A$ represents a value of x on the aspherical surface corresponding to an optimal value of y; and $X_S$ designates a value of x on the reference sphere corresponding to said value of y.

5. An optical system for an endoscope according to claim 4 wherein:
said second lens unit comprises a first positive subunit and a second positive subunit.

6. An optical system for an endoscope according to claim 4 wherein:
said second lens unit comprises a positive subunit and a negative subunit.

7. An optical system for an endoscope according to claim 1, wherein said second lens unit comprises:
a positive lens component having a convex surface on an image side thereof;
a positive cemented lens component; and
a cemented lens component.

8. An optical system for endoscopes according to claim 7, wherein:
said positive cemented lens component has a concave surface on an object side thereof; and
said cemented lens component has a convex surface on an object side thereof and a positive refractive power.

9. An optical system for an endoscope according to claim 7, wherein:
said positive cemented lens component has a biconvex shape; and
said cemented lens component has a convex surface on an object side thereof and a positive refractive power.

10. An optical system for an endoscope according to claim 7, wherein:
said positive cemented lens component has a biconvex shape; and
said cemented lens component has a biconcave shape.

11. An optical system for an endoscope according to claim 7, wherein:
said positive cemented lens component has a convex surface on an image side thereof; and
said cemented lens component has a concave surface on an object side thereof.

* * * * *